US011382526B2

(12) United States Patent
Vogel et al.

(10) Patent No.: US 11,382,526 B2
(45) Date of Patent: Jul. 12, 2022

(54) SYSTEM AND METHOD FOR GENERATING A TRAVELING FIELD FREE LINE

(71) Applicant: Julius-Maximilians-Universität Würzburg, Würzburg (DE)

(72) Inventors: Patrick Vogel, Gerbrunn (DE); Martin Rückert, Reichenberg (DE); Volker Christian Behr, Gerbrunn (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 104 days.

(21) Appl. No.: 17/041,969

(22) PCT Filed: Feb. 28, 2019

(86) PCT No.: PCT/EP2019/055061
§ 371 (c)(1),
(2) Date: Sep. 25, 2020

(87) PCT Pub. No.: WO2019/185292
PCT Pub. Date: Oct. 3, 2019

(65) Prior Publication Data
US 2021/0137407 A1 May 13, 2021

(30) Foreign Application Priority Data
Mar. 29, 2018 (EP) .................................... 18165054

(51) Int. Cl.
*A61B 5/0515* (2021.01)
*G01R 33/20* (2006.01)
(52) U.S. Cl.
CPC ............ *A61B 5/0515* (2013.01); *G01R 33/20* (2013.01)
(58) Field of Classification Search
CPC .............................. A61B 5/0515; G01R 33/20
See application file for complete search history.

(56) References Cited

U.S. PATENT DOCUMENTS 6,921,042 B1  7/2005  Goodzeit et al.
7,351,194 B2 *  4/2008  Gleich ................... A61N 1/406
                                                        600/12

(Continued)

FOREIGN PATENT DOCUMENTS

WO     WO 2011/021165 A1      2/2011

OTHER PUBLICATIONS

Chandrasekharan et al.; "A perspective on a rapid and radiation-free tracer imaging modality, Magnetic Particle Imaging, with promise for clinical translation"; The British journal of radiology 91(4):20180326; (2018); pp. 1-14.*

(Continued)

*Primary Examiner* — Dixomara Vargas
(74) *Attorney, Agent, or Firm* — Sunstein LLP

(57) ABSTRACT

A system for generating a traveling field free line, traveling along a propagation direction different from the orientation of said traveling field free line, said system comprising at least a first and a second coil assembly, wherein said first coil assembly is configured for generating a first stationary field free line at a first location when a current is flowing in the first coil assembly and the second coil assembly is current free, and wherein said second coil assembly is configured for generating a second stationary field free line at a second location, when a current is flowing in the second coil assembly and the first coil assembly is current free. The system further comprises a controller configured for driving the first and second coil assemblies with corresponding driving currents synchronized with each other, such that said traveling field free line travels along the propagation direction from a first location towards a second location.

20 Claims, 14 Drawing Sheets

(56) References Cited

U.S. PATENT DOCUMENTS

| | | | | |
|---|---|---|---|---|
| 10,267,873 | B2* | 4/2019 | Gleich | G01R 33/28 |
| 10,478,087 | B2* | 11/2019 | Top | G01R 33/1276 |
| 2010/0045281 | A1* | 2/2010 | Gleich | G01R 33/12 |
| | | | | 324/239 |
| 2012/0058441 | A1* | 3/2012 | Boeve | G01R 33/1276 |
| | | | | 432/36 |
| 2017/0067972 | A1* | 3/2017 | Diamond | G01R 33/1276 |
| 2018/0231629 | A1* | 8/2018 | Top | G01R 33/1276 |
| 2018/0335487 | A1* | 11/2018 | Tonyushkin | A61B 5/0515 |

OTHER PUBLICATIONS

Straub et al.; "MPI field generator design for an FFL based image acquisition"; IEEE Xplore; (2022); https://ieeexplore.ieee.org/stamp/stamp.jsp?arnumber=7107056.*

International Searching Authority/EP, International Search Report and Written Opinion of the International Searching Authority, Application No. PCT/EP2019/055061, dated Jun. 3, 2019, 16 pages.

Marlitt Erbe, "Chapter 3 Introduction of a Field Free Line for Magnetic Particle Imaging," from *Field Free Line Magnetic Particle Imaging*, Mar. 12, 2014, Sprinter Vieweg, XP002785347, ISBN: 978-3-658-05336-9 pp. 43-59.

Can Baris Top et al., "Electronically rotated and translated field-free line generation for open bore magnetic particle, imaging," Med. Phys, 44 (12) Dec. 2017, XP055511266, pp. 6225-6238.

C. Khulmann et al., "A 3D MPI System for Biological Studies on Mice," 2013 International Workshop on Magnetic Particle Imaging (IWMPI), Berkeley, CA, 2013, pp. 1-1, doi: 10.1109/IWMPI.2013. 6528373.

Patrick Vogel et al., "Traveling Wave Magnetic Particle Imaging," IEEE Transactions on Medical Imaging, vol. 22, No. 2, Feb. 2014 pp. 400-407.

P. Vogel et al., "Dynamic Linear Gradient Array for Traveling Wave Magnetic Particle Imaging," IEEE Transactions on Magnets, vol. 54, No. 2, pp. 1-9, Feb. 2018, Art No. 5300109, doi: 10.1109/TMAG.2017.2764440.

Juergen Weizenecker et al., "Magnetic particle imaging using a field free line," J. Phy. D: Appl. Phys. 41 (2008) doi: 10.1088/0022-3727/41/10/105009, pp. 1-3.

Klaas Bente et al., "Electronic Field Free Line Rotation and Relaxation Deconvolution in Magnetic Particle Imaging," IEEE Trans Med Imaging. 2015;34(2):644-651. doi:10.1109/TMI.2014.2364891.

C.L. Goodzeit et al., "The Double-Helix Dipole—A Novel Approach to Accelerator Magnet Design," IEEE Translations on Applied Superconductivity, vol. 13, No. 2, Jun. 2003, pp. 1365-1368.

R. Matthew Ferguson et al., "Magnetic Particle Imaging with Tailored Iron Oxide Nanoparticle Tracers," IEEE Trans Med Imaging. 2015;34(5), pp. 1-9, doi:10.1109/TMI.2014.2375065.

Bernhard Gleich et al. "Tomographic imaging using the nonlinear response of magnetic particles," Nature 435, 1214-1217 (2005); https://doi.org/10.1038/nature03808.

T. Knopp et al., "Magnetic particle imaging: from proof of principle to preclinical applications," Phy. Med. Biol. 62 (2017) R124-R178; https://doi.org/10.1088/1361-6560/aa6c99.

Emine U. Saritas et al., "Magnetic Particle Imaging (MPI) for NMR and MRI researchers," J. Magn. Reson. (2013), pp. 1-11, http://dx.doi.org/10.1016/j.jmr.2012.11.029.

Patrick. W. Goodwill et al., "Projection X-Space Magnetic Particle Imaging," *IEEE Transactions on Medical Imaging*, vol. 31, No. 5, pp. 1-11, May 2012, doi: 10.1109/TMI.2012.2185247.

* cited by examiner

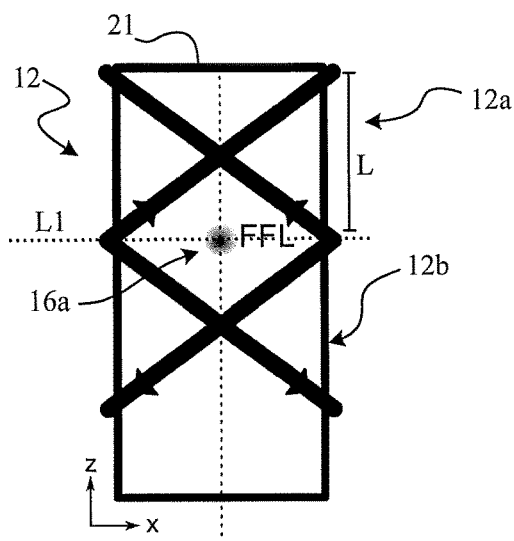
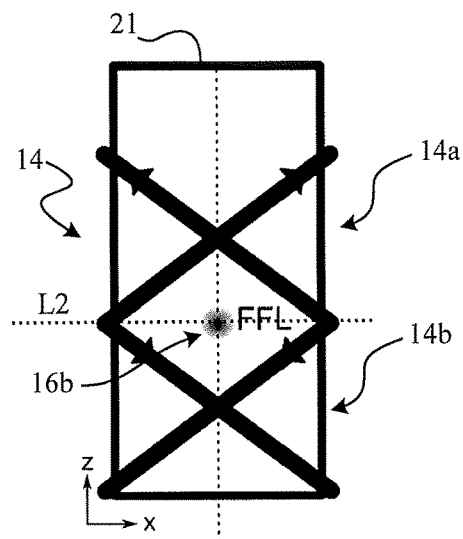
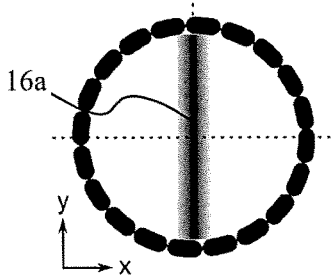
Fig. 6A
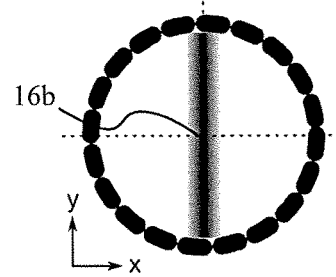
Fig. 6B
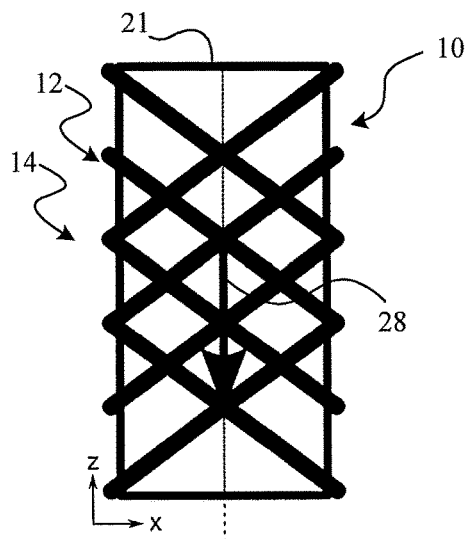
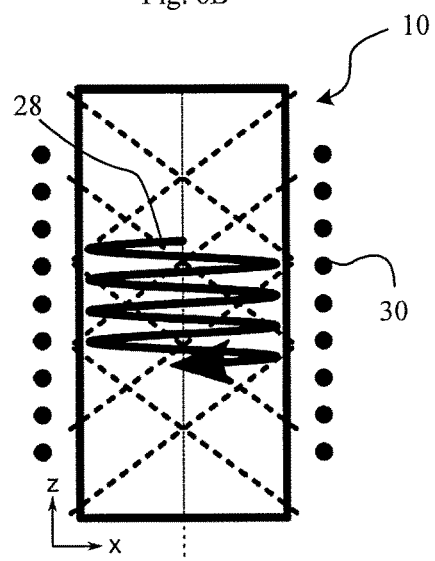
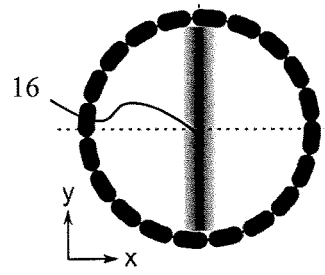
Fig. 6C
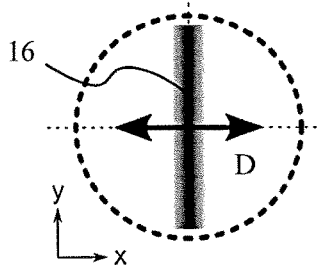
Fig. 6D

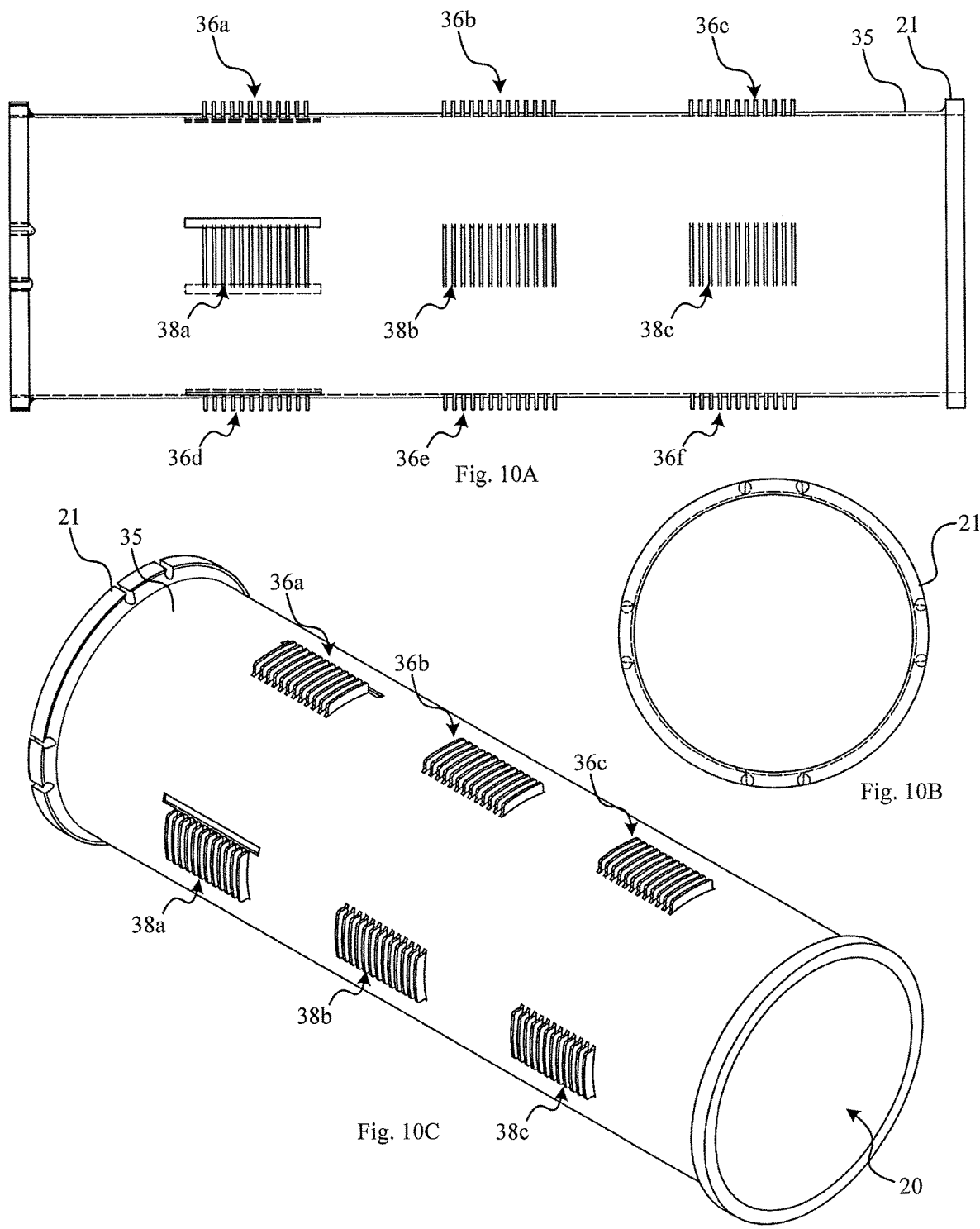

SYSTEM AND METHOD FOR GENERATING A TRAVELING FIELD FREE LINE

CROSS-REFERENCE TO RELATED APPLICATIONS

This application is the national phase entry of International Patent Application No. PCT/EP2019/055061 filed on Feb. 28, 2019, and claims the benefit of European Patent Application No. 18165054.0 filed Mar. 29, 2018, the disclosures of which are incorporated herein by reference in their entirety.

FIELD OF THE INVENTION

The present invention is in the field of magnetic imaging technology. More precisely, the present invention relates to magnetic particle imaging using magnetic field free lines.

BACKGROUND

The treatment and diagnosis of medical conditions increasingly relies on imaging technology. Commonly used methods such as X-ray Computed Tomography (CT) and Positron Emission Tomography (PET) provide fast acquisition times with high spatial resolution but expose the patient to high-energy radiation.

In contrast, magnetic imaging technology uses the characteristic response of atoms, molecules or particles in the human body to a time varying magnetic field distribution to provide three-dimensional images of the patient's body. For example, nuclear magnetic resonance (NMR) uses the response of hydrogen atoms in the patient's body to microwave fields applied alongside magnetic field gradients to infer the concentration and the position of the hydrogen atoms in the patient's body and can be used to provide a three-dimensional image of the tissue composition of the patient.

Magnetic particle imaging (MPI) is an imaging technique which has been recently proposed by Gleich et al. ("*Tomographic imaging using the nonlinear response of magnetic particles*" in *Nature Letters*, June 2005) as a radiation-free diagnosis tool. In this technique, small magnetic particles, such as iron oxide particles with a diameter in a range of 10 to 40 nm, are introduced into the body of the patient and the response of these particles to time varying magnetic fields is used to infer their concentration and position. In particular, Gleich et al. proposed using a magnetic field free point (FFP) at which the magnetization of the particles can be switched with a low amplitude time-varying magnetic field, while outside of the magnetic FFP, the time-varying magnetic field does not produce any significant magnetization change. By moving the magnetic FFP within the probe volume and recording the magnetic response to said time-varying magnetic field, a three-dimensional image of the concentration of the small magnetic particles can be produced. By functionalizing the magnetic particles, even specific molecules or cells can be traced throughout the body of the patient. Weizenecker et al. ("*Magnetic particle imaging using a field free line*" in *J. Phys. D: Appl. Phys.* 41, May 2008) theoretically showed that a two-dimensional image of the magnetic particle distribution can be created by inducing a magnetic field free line (FFL) in an investigated two-dimensional plane, which is subsequently rotated as well as laterally translated to infer the magnetic particle distribution and concentration with image reconstruction schemes similar to the ones used in CT. By moving the patient through the apparatus, a three-dimensional magnetic particle distribution can be inferred from a series of two-dimensional slices.

In a theoretical study, Top et al. ("Electronically rotated and translated field-free line generation for open bore magnetic particle imaging", in Medical Physics, vol. 44, December 2017) proposed a magnetic field coil arrangement to generate a rotatable and translatable FFL in a two-dimensional plane between oppositely arranged coil assemblies, wherein a three-dimensional field of view can be scanned by varying the current magnitude in the oppositely arranged coil assemblies and thereby electrically changing the investigated two-dimensional plane by introducing an additional magnetic field gradient between the oppositely arranged coil assemblies. However, due to a smearing-out of the field free line farther away from the central position of the field free line, the electrical power required to image the edges of the field of view are increased by up to a factor of 3.5.

Vogel et al. ("*Dynamic Linear Gradient Array for Traveling Wave Magnetic Particle Imaging*", in *IEEE Transactions on Magnetics*, vol. 54, February 2018) have proposed a displacement scheme for a field free point, wherein the extension of possible displacement is increased along one axis, by using an array of concatenated and synchronized Maxwell coils.

SUMMARY OF THE INVENTION

The known methods and corresponding devices for providing three-dimensional images of the magnetic particle response can be divided into two separate approaches. Using a field free point, an electrically driven three-dimensional scanning of a field of view has already been put into practice. However, the signal-to-noise ratio in the FFP approach limits the applicability of the technique. A higher magnetic response signal can be provided using a field free line. However, reliable displacement of the field free line along several axes still relies on mechanical displacements or involves conceptual compromises regarding resolution or size of the field of view.

Thus, the object underlying the invention is to provide a scalable system and method for generating a field free line, which can be efficiently displaced to scan a two- or three-dimensional probe volume without involving mechanical displacement in order to achieve large field-of-view and/or fast acquisition times for reliable magnetic imaging applications.

This object is solved by a system and method according to the independent claims. The dependent claims relate to preferred embodiments. The invention is in the following described with reference to use in medical diagnosis and imaging, but may also find applications in different fields benefiting from spatially resolved density information on magnetizable particles, such as biological research or the investigation of material composition or workpieces.

If not explicitly mentioned, any gradients, field strengths and field free regions should be considered to relate to magnetic field gradients, magnetic field strengths and magnetic field free regions. Particularly, for the sake of convenience, a magnetic field free line will be referred to as "FFL" or "field free line". Such a field free line defines, along its extension direction, a columnar region with a magnetic field strength smaller than the magnetic saturation field to magnetically saturate the investigated magnetizable particles or magnetizable portions, and is defined within a region having a magnetic field strength above said magnetic saturation field, such as being defined in a region having the shape of a hollow cylinder and having a magnetic field strength above said magnetic saturation field outside of the hollow portion of the cylinder. It is noted that in real physical systems, a full magnetic saturation may only be achieved approximately. Hence, the magnetic saturation field can be considered to be the field above which the particle shows substantially paramagnetic response to magnetic field changes, i.e. above which the relation between magnetizing field and magnetic field at or close to the particle levels off and is substantially linear. Thus, a non-linear response of the magnetic field to an externally applied magnetizing field can be attributed to the location of the field free line.

Hence, by generating such a field free line, the response of the magnetizable particles at or close to the field free line to a time-varying magnetic field can be investigated within a defined spatial volume. By displacing the field free line, a probe volume can be scanned with the field free line to infer a spatial dependence of said response within the probe volume. Naturally, the field free line need not be straight.

The probe volume as well as any scanned planes and scanned three-dimensional regions will in the following be described according to characteristic positions relating to the coil elements used in the system and associated methods. Nevertheless, the probe volume, which can be scanned by the different embodiments, usually extends beyond said defining characteristic positions and can be reduced as needed by limiting the current amplitudes in the different coil assemblies in accordance with their function or can be partitioned by modulating the currents in a step-wise manner. Hence, the described translation and modulation sequences should be considered illustrative rather than limiting.

According to a first aspect, the invention relates to a system for generating a traveling field free line, traveling along a propagation direction different from the orientation of said field free line. The system comprises at least a first and a second coil assembly. Said first coil assembly is configured for generating a first stationary field free line at a first location when a current is flowing in the first coil assembly and the second coil assembly is current free. The second coil assembly is configured for generating a second stationary field free line at a second location, when a current is flowing in the second coil assembly and the first coil assembly is current free. The system further comprises a controller configured for driving the first and second coil assemblies with corresponding driving currents synchronized with each other such that:
  at a first point in time, the first coil assembly's driving current amplitude is high and the second coil assembly's driving current amplitude is low, such that at said first point in time the traveling field free line is at or close to said first location,
  at a second point in time, the second coil assembly's driving current amplitude is high and the first coil assembly's driving current amplitude is low, such that at said second point in time the traveling field free line is at or close to said second location, and
  in a time interval between said first and second point in time, the amplitude of the first driving current in the first coil assembly decreases and the amplitude of the second driving current in the second coil assembly increases as compared to said first point in time such that said traveling field free line travels along the propagation direction from said first location towards said second location.

The traveling field free line can be translated between said first location and said second location along the propagation direction by adjusting the current amplitudes in the first and second coil assemblies. The current amplitude may be a magnitude of a DC or slowly varying current or may relate to the amplitude of a time varying current modulation, such as an AC current amplitude, or the amplitude of an envelope of a time varying current modulation.

The first and second stationary field free lines act as characteristic positions of the traveling field free line through which the traveling field free line may be translated along a translatory movement. Along the translatory movement, the traveling field free line can scan a two-dimensional plane between the first and second stationary field free line, such as a flat surface or a helicoidal surface spanned by the first and second stationary field free lines.

As each of the first and second coil assemblies are configured for generating an associated stationary field free line, the gradient distribution of the field free line at the characteristic positions can be well defined by the respective coil assemblies. Hence, when a two-dimensional plane is scanned by the traveling field free line, a well-defined gradient can be produced at said stationary field free line positions close to the edges of the two-dimensional plane.

In some embodiments, the first and second coil assemblies overlap along the propagation direction, when viewed from a direction perpendicular to the propagation direction, such as to generate the traveling field free line traveling along the propagation direction between the first and second locations with a given minimum magnetic field gradient across the lateral extension of the traveling field free line or with a low dispersion/warping of the traveling field free line along the propagation direction. In some embodiments, an edge of the first coil assembly is at or close to the second location, such as to generate a traveling field free line with a low gradient dispersion along a trajectory between the first and second locations by varying the current amplitude in the first and second coil assemblies.

Preferably, the first and second coil assemblies are configured to define a through-going passage extending between the locations of the first and second stationary field free lines. The through-going passage can be adapted to introduce and/or accommodate an investigated sample, such that by generating the traveling field free line, the sample in the through-going passage can be scanned with the traveling field free line. Particularly, by periodically modulating the current amplitude in the first and second coil assemblies, the traveling field free line may be repeatedly translated through the through-going passage past the first location and the second location in a direction from the first to the second location, or vice-versa, or back-and-forth.

In a preferred embodiment, the system further comprises a measurement coil for recording a non-linear response of an at least partially magnetizable system located in a probe volume between the first location and the second location to obtain a measurement of a density and/or a distribution of magnetizable particles in the at least partially magnetizable system.

The at least partially magnetizable system may be an investigated sample comprising a distribution of magnetizable particles. The magnetic field gradient distribution at or close to the position of the field free line should be suitable to change the magnetization of the magnetizable particles by the passage of the traveling field free line within a given volume around the magnetizable particles. The measurement coil may be configured to measure a magnetic signal originating from the magnetization change of the particles in the investigated sample at or close to the traveling field free line in response to a magnetic excitation generated by the system, which magnetic excitation may correspond to the passage of the field free line.

Particularly, reversing the magnetization of a magnetizable particle with a given drive frequency may produce a higher harmonic excitation with respect to the drive frequency due to a non-linearity of the magnetization curve of the magnetizable particle below the saturation field of said particle. Hence, a higher harmonic signal measured with the measurement coil can be attributed to a signal originating from the field free region defined by the traveling the field free line.

In other words, the measurement coil may allow a projective measurement along the field free line, the signal originating from the field free line depending on the summed nonlinear response of the magnetizable particles at or close to the field free line. By frequency filtering the magnetic signal picked up by the measurement coil, such as by using a band-pass or high-pass filter connected to the measurement coil, a linear response of portions of the investigated sample or the apparatus may be discerned from a nonlinear response of magnetizable particles along the field free line, the nonlinear response of the magnetizable particles originating from a magnetization change of the magnetizable particles.

In a preferred embodiment, the system further comprises a deflection coil assembly, the deflection coil assembly being adapted for generating a deflection magnetic field. The controller is adapted to modulate the deflection magnetic field with a deflection frequency for displacing the traveling field free line along a deflection direction, the deflection direction being different from the propagation direction to allow for an arbitrary displacement of the traveling field free line on an investigated two-dimensional plane defined by the propagation direction and the deflection direction.

In this way, a projective measurement along the extension of the traveling field free line, onto the surface of said investigated two-dimensional plane can be performed, such as a parallel projection of the magnetizable portions of an investigated sample onto said investigated two-dimensional plane.

In preferred embodiments, the deflection direction is perpendicular to the propagation direction and/or the orientation of the traveling field free line, or deviates from being perpendicular to the propagation direction and/or the orientation of the traveling field free line by less than 30°, preferably less than 10°.

The deflection coil assembly is preferably adapted for generating an axial magnetic field parallel to the propagation direction. For example, the deflection coil assembly may comprise a solenoid coil aligned along the propagation direction. Thus, a substantially uniform magnetic field may be generated in a through-going passage through the first and second coil assemblies, such as to facilitate a substantially uniform deflection of the traveling field free line independently of the current position of the traveling field free line along the propagation direction.

In some embodiments, the current through the deflection coil is periodically modulated to induce a periodic magnetization reversal at or close to the traveling field free line along the deflection direction, such as to generate a magnetic excitation within a slice of an investigated sample, the slice being defined by the traveling field free line and the deflection direction.

In some embodiments, the deflection coil and the measurement coil relate to the same physical coil and respective drive/measurement signals are distinguished by frequency filtering of the current in the coil.

The shape and arrangement of the deflection and measurement coils may be chosen from any known coil shape suitable to perform the above-described function. In some embodiments, the deflection coil and/or the measurement coil relate to any one of a closed loop, solenoid, TEM, saddle, or birdcage coil, or to similar or derived coil shapes. However, it is noted that a conductor of virtually any physical shape and orientation may be suitable for implementing the measurement coil.

In preferred embodiments, the through-going passage along the propagation direction to accommodate an investigated sample extends beyond the space spanned between locations of the first and second stationary field free lines, such as through the first and second coil assemblies. For example, the first and second coil assemblies may define an open bore along the propagation direction. In this way, any of the coil assemblies of the system, such as the first coil assembly, can be replicated along the propagation direction, and the propagation distance of the traveling field free line along the propagation direction can be extended as needed. Moreover, a combination of three spaced apart coil assemblies, such as the first or second coil assemblies, arranged along the propagation direction can produce at least two synchronized propagating traveling field free lines to provide parallel scanning of a sample in a through-going passage aligned along the propagation direction.

When generating at least two traveling field free lines, a measurement assembly of at least two measurement coils may be used to discern the spatial origin of a magnetization signal originating from an investigated sample between the at least two traveling field free lines.

In a preferred embodiment, the system further comprises a third and a fourth coil assembly. The third coil assembly is configured for generating a third stationary field free line at a third location, when a current is flowing in the third coil assembly and the first, second and fourth coil assemblies are current free. The fourth coil assembly is configured for generating a fourth stationary field free line at a fourth location, when a current is flowing in the fourth coil assembly and the first, second and third coil assemblies are current free. The first and third coil assemblies are arranged with respect to each other such that the first and third stationary field free lines form a nonzero angle, said nonzero angle in particular deviating from 90° by less than 45°, preferably by less than 30°, most preferably by less than 10°. The second and fourth coil assemblies are arranged with respect to each other such that the second and fourth stationary field free line form a nonzero angle, said nonzero angle in particular deviating from 90° by less than 45°, preferably by less than 30°, most preferably by less than 10°. Additionally, the controller is configured to drive the first through fourth coil assemblies such as to generate a field free line at a desired position along the propagation direction and at a desired orientation.

By providing a first pair of coil assemblies comprising the first and second coil assemblies and a second pair of coil assemblies comprising the third and fourth coil assemblies, which can provide different orientations of a traveling field free line, the superposition of the magnetic fields of the first and second pairs of coil assemblies can be used to generate a magnetic field free line at a desired orientation.

An investigated space between the third location and the fourth location should preferably overlap with an investigated space between the first location and the second location. Preferably, the third location is at or close to the first location and the fourth location is at or close to the second location. Since each of the first and second pairs of coil assemblies provide translation of the traveling field free line along the propagation direction but with different orientations, a traveling field free line with a desired orientation may be translated through a through-going passage defined by both the first and second as well as the third and fourth coil assemblies along the propagation direction.

In some embodiments, the structure of the third and fourth coil assemblies and/or their spatial position are similar or identical to the structure and/or spatial position of said first and second coil assemblies but are each rotated about the propagation direction by said nonzero angle. In these examples, the first and third stationary field free lines as well as the second and fourth stationary field free lines each define substantially elliptical slices of a cylindrical probe volume arranged along the propagation direction which can be scanned with the traveling field free line.

In a preferred embodiment, the first and second stationary field free lines are oriented along a first radial direction with respect to said propagation direction, and the third and fourth stationary field free lines are oriented along a second radial direction with respect to said propagation direction. The first and second radial directions form an angle deviating from 90° by less than 30°, most preferably by less than 10°.

In a preferred embodiment, the controller is further configured for inducing a helicoidal displacement of the traveling field free line by varying the respective current amplitude in a first pair of coil assemblies comprising the first and second coil assemblies and in a second pair of coil assemblies comprising the third and fourth coil assemblies, such that at times between said first and second point in time, the current amplitude in the first pair of coil assemblies decreases and the current amplitude in the second pair of coil assemblies increases.

The helicoidal displacement relates to a helicoidal or spiral surface which the traveling field free line lies in while being translated along the propagation direction, such as by modulating the current amplitudes in the first through fourth coil assemblies with periodic functions.

In some embodiments including the third and fourth coil assemblies, the deflection coil assembly is configured to provide a radial deflection of the traveling field free line in a deflection direction, which is perpendicular to the orientation of the traveling field free line and is different from the propagation direction.

Thus, a plurality of measurement slices may be scanned with different orientations of the traveling field free line for each investigated position along the propagation direction of the traveling field free line. The nonlinear response of magnetizable particles within the slices may be measured and combined to infer a three-dimensional image of the nonlinear magnetic response of an investigated sample within the probe volume.

In a preferred embodiment, the controller is configured to vary the current amplitude $A_1$ in the first coil assembly according to $A_1 = a_1 * f_1^{\omega_1}(t) * f_2^{\omega_2}(t)$,
vary the current amplitude $A_2$ in the second coil assembly according to $A_2 = a_2 * f_1^{\omega_1}(t+\varphi_1) * f_2^{\omega_2}(t)$,
vary the current amplitude $A_3$ in the third coil assembly according to $A_3 = a_3 * f_3^{\omega_1}(t) * f_2^{\omega_2}(t+\varphi_3)$, and
vary the current amplitude $A_4$ in the fourth coil assembly according to $A_4 = a_4 * f_3^{\omega_1}(t+\varphi_2) * f_2^{\omega_2}(t+\varphi_3)$.
The functions $f_1^{\omega_1}$, $f_2^{\omega_2}$ and $f_3^{\omega_1}$ are hereby periodic functions in time with a periodicity of $f_1^{\omega_1}$ and $f_3^{\omega_1}$ of $2\pi/\omega_1$, and a periodicity of $f_2^{\omega_2}$ of $2\pi/\omega_2$. For example, $f_1^{\omega_1}$, $f_2^{\omega_2}$ and $f_3^{\omega_1}$ may be trigonometric functions, such as sine or cosine functions. The pre-factors $a_1$ to $a_4$ are proportionality constants, and t relates to time. The angular velocity $\omega_1$ relates to a first frequency, the first frequency relating to a propagation time of the traveling field free line between the first and second location during a displacement of the traveling field free line along the propagation direction between the first and second point in time. The angular velocity cot relates to a second frequency, the second frequency relating to a rotation time of the traveling field free line about the propagation direction during the displacement of the traveling field free line along the propagation direction. The phase shifts $\varphi_1$ and $\varphi_2$ relate to phase shifts preferably deviating from $\pi/2\omega_1$ by less than $\pi/4\omega_1$ in particular by less than $\pi/6\omega_1$, preferably by less than $\pi/18\omega_1$, and the phase shift $\varphi_3$ relates to a phase shift preferably deviating from $\pi/2\omega_2$ by less than $\pi/4\omega_2$ in particular by less than $\pi/6\omega_2$, preferably by less than $\pi/18\omega_2$.

Particularly, the first and second frequencies should be different from each other to scan each investigated position of the probe volume along the propagation direction with a number of different orientations of the traveling field free line. For example, when $f_1^{\omega_1}$, $f_2^{\omega_2}$ and $f_3^{\omega_1}$ are sine or cosine functions and $\varphi_1$, $\varphi_2$ and $\varphi_3$ relate to phase shifts of said functions by $\pi/2$, a helicoidal displacement of the traveling field free line along the propagation direction can be achieved.

When using a phase shift $\varphi_1$, $\varphi_2$ and $\varphi_3$, which is different from $\pi/2$ and also differs from 0 and $\pi$, the trajectory of the traveling field free line may be modified, such that the traveling field free line may travel non-linearly through the probe volume, such as to spend more time in a certain portion of the probe volume. Thus, by choosing a phase shift $\varphi_1$, $\varphi_2$ and/or $\varphi_3$ different from $\pi/2$, a zoom on the certain portion of the probe volume may effectively be achieved. Hence, in some embodiments, the phase shifts $\varphi_1$, $\varphi_2$ and/or $\varphi_3$ between periodic modulations of the current amplitudes in different coil assemblies are different from 0 and $\pi$.

In a preferred embodiment, the first coil assembly and the second coil assembly each comprise a first tilted Maxwell coil assembly and a second tilted Maxwell coil assembly. The tilted Maxwell coil assemblies comprise two coils arranged in parallel planes and connected to be driven by opposite driving currents, said Maxwell coil assemblies defining a normal that is orthogonal to said parallel planes. The first and second Maxwell coil assemblies are arranged such that their respective normals form a nonzero tilt angle with the propagation direction and are further arranged such that the normal of the first tilted Maxwell coil assembly and the normal of the second tilted Maxwell coil assembly form an angle, the angle being 90° or deviating from 90° by less than 45°, in particular by less than 30°, preferably by less than 15°.

The term Maxwell coil assembly should not be construed as to imply any limitation on the distance between the above-mentioned two coils. Rather, the term is considered to merely imply the presence of two coils arranged in parallel planes which are driven by opposite driving currents. Such a coil arrangement can produce a magnetic field gradient between said two coils.

A single Maxwell coil assembly can produce a field free point at a middle location between the two coils. However, combining two tilted Maxwell coils, a field free line may be generated at a common middle location of the two tilted Maxwell coil assemblies. Preferably, the two tilted Maxwell coils form two pairs of crossed coils, the crossed coils relating to overlapping coils of the first and second tilted Maxwell coil assemblies whose parallel planes intersect at a middle location of each coil of the crossed coils.

Hence, the normals of the first and second tilted Maxwell coil assemblies may form an angle being equal to the sum of the absolute value of the respective tilt angles of the first and second Maxwell coil assemblies.

In a preferred embodiment, the system comprises a cylindrical coil carrier having an axis aligned with the propagation direction, wherein the coils of the first and second tilted Maxwell coil assemblies are wound on the cylindrical coil carrier, and the first tilted Maxwell coil assembly and the second tilted Maxwell coil assembly share at least one common coil wire. Particularly, one common coil wire may be used to form one coil of each pair of crossed coils, the coils being associated with different tilted Maxwell coil assemblies. Such a winding may produce a dense wiring on said cylindrical coil carrier with the edges of the two crossed coil assemblies overlapping at a middle position. In principle, one common coil wire may be used for winding both the first and second tilted Maxwell coil assemblies.

In some embodiments, the first coil assembly comprises first and second portions, such as the two pairs of crossed coils, the magnetic field generated individually by said first and second portions at respective middle locations of the first and second portions being substantially transverse with respect to the propagation direction, such as forming a nonzero angle with the propagation direction, the angle being greater than 60°, wherein between said respective middle locations, the direction of the magnetic field generated by cooperating first and second portions reverses sign at the first location to generate the first stationary field free line. Particularly, the centers of the first and second portions may be translated along the propagation direction with respect to each other.

In a related second aspect, the invention relates to a method of generating a traveling field free line using at least a first and a second coil assembly, wherein said traveling field free line travels along a propagation direction different from the orientation of said field free line. The first coil assembly is configured for generating a first stationary field free line at a first location when a current is flowing in the first coil assembly and the second coil assembly is current free. The second coil assembly is configured for generating a second stationary field free line at a second location, when a current is flowing in the second coil assembly and the first coil assembly is current free. The method comprises driving the first and second coil assemblies with corresponding driving currents synchronized with each other such that:
- at a first point in time, the first coil assembly's driving current amplitude is high and the second coil assembly's driving current amplitude is low, such that at said first point in time the traveling field free line is at or close to said first location,
- at a second point in time, the second coil assembly's driving current amplitude is high and the first coil assembly's driving current amplitude is low, such that at said second point in time the traveling field free line is at or close to said second location, and
- in a time interval between said first and second point in time, the amplitude of the first driving current in the first coil assembly decreases and the amplitude of the second driving current in the second coil assembly increases as compared to said first point in time such that said traveling field free line travels along the propagation direction from said first location towards said second location.

In a preferred embodiment, the method further uses at least a third and a fourth coil assembly. The third coil assembly is configured for generating a third stationary field free line at a third location, when a current is flowing in the third coil assembly and the first, second and fourth coil assemblies are current free. The fourth coil assembly is configured for generating a fourth stationary field free line at a fourth location, when a current is flowing in the fourth coil assembly and the first, second and third coil assemblies are current free. The first and third stationary field free lines form a nonzero angle, said nonzero angle in particular deviating from 90° by less than 45°, preferably by less than 30°, most preferably by less than 10°. The second and fourth stationary field free lines form a nonzero angle, said nonzero angle in particular deviating from 90° by less than 45°, preferably by less than 30°, most preferably by less than 10°. Additionally, the method further comprises driving the first through fourth coil assemblies such as to generate a field free line at a desired position along the propagation direction and at a desired orientation.

In some preferred embodiments, the method further comprises inducing a helicoidal displacement of the traveling field free line by varying the respective current amplitude in a first pair of coil assemblies comprising the first and second coil assemblies and in a second pair of coil assemblies comprising the third and fourth coil assemblies, such that at times between said first and second point in time, the current amplitude in the first pair of coil assemblies decreases and the current amplitude in the second pair of coil assemblies increases.

In some embodiments, the method further comprises generating a deflection magnetic field, in particular an axial magnetic field parallel to the propagation direction, preferably using a deflection coil assembly comprising a solenoid coil, and most preferably varying the magnitude of the deflection magnetic field with a deflection frequency, to displace the traveling field free line in a radial direction perpendicular to the propagation direction.

In a preferred embodiment, the method further comprises recording, with a measurement coil, a non-linear response of an at least partially magnetizable system located in a probe volume between the first location and the second location to obtain a measurement of a density and/or a distribution of magnetizable particles in the at least partially magnetizable system.

In some embodiments, the method is further adapted for controlling or providing the function of any one of the embodiments of the system according to the first aspect or their combinations.

In a related third aspect, the invention relates to a computer program or computer program product comprising machine readable instructions, which when executed, cause a computer to control a system according to the first aspect, or to implement a method according to the second aspect, a combination of the two, or to control or implement any of their embodiments described above.

DETAILED DESCRIPTION OF EMBODIMENTS

The features and numerous advantages of the system and method for generating a traveling field free line according to the present invention will best be understood from a detailed description of preferred embodiments with reference to the accompanying drawings, in which:

FIG. 6A shows schematic top and side views of a first coil assembly for generating a first stationary field free line with two tilted Maxwell coil assemblies in a crossed coil configuration according to an example;

FIG. 6B shows schematic top and side views of an associated second coil assembly for generating a second stationary field free line with two tilted Maxwell coil assemblies in a crossed coil configuration according to an example;

FIG. 6C shows a system for generating a traveling field free line in accordance with the first and second coil assemblies shown in FIGS. 6A and 6B according to an example;

FIG. 6D illustrates the translatory movement of a traveling field free line in the system of FIG. 6C combined with a deflection coil according to an example;

FIG. 10 illustrates a cylindrical coil carrier for carrying a first coil assembly for generating a stationary field free line according to an example;

Figure 1:
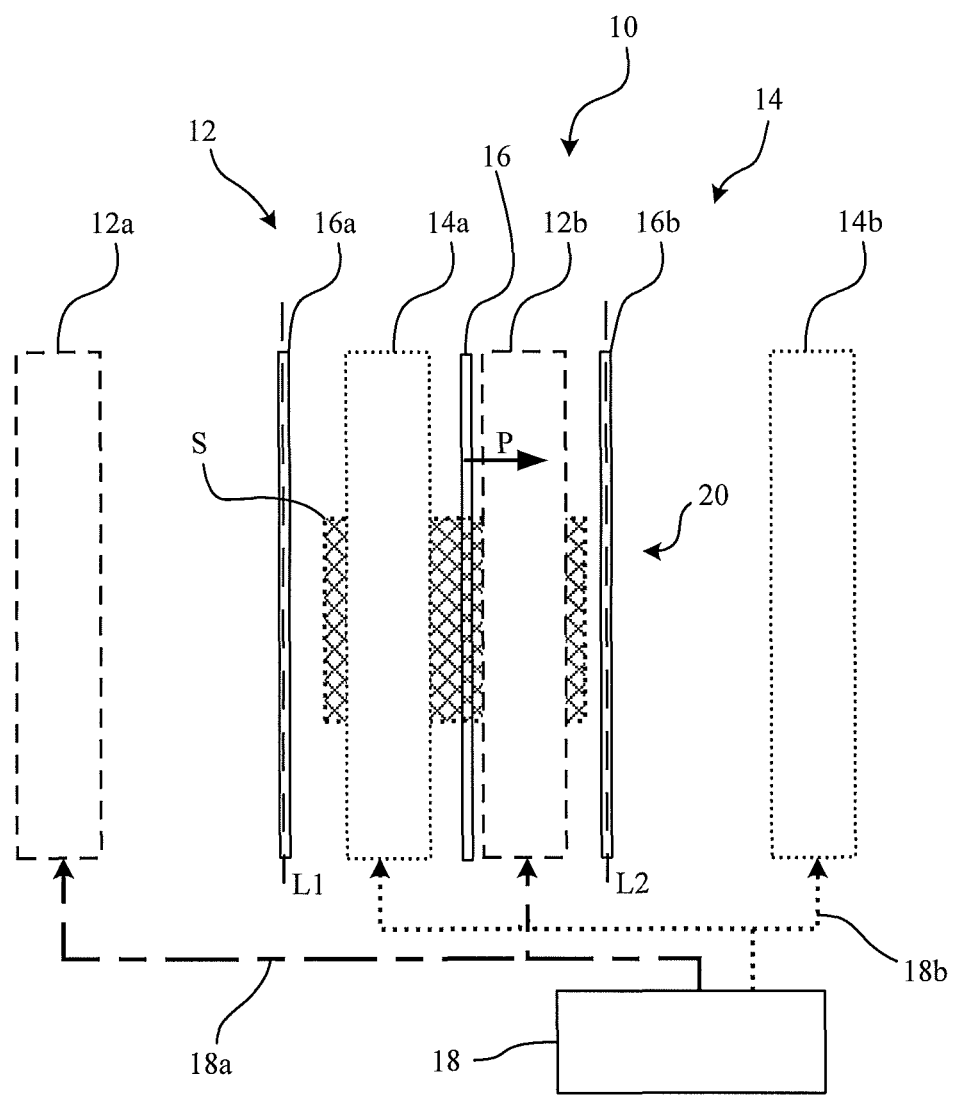
FIG. 1 is a schematic illustration of a system for generating a traveling field free line according to an example.

FIG. 1 shows an embodiment of a system 10 for generating a traveling field free line 16, the traveling field free line 16 traveling along a propagation direction P different from the orientation of said field free line 16. The system 10 comprises a first coil assembly 12 and a second coil assembly 14, each comprising first portions 12a, 14a and second portions 12b, 14b. The first and second portions 12a, 12b of the first coil assembly 12 cooperate to generate a first stationary field free line 16a at a first location L1 when a current is flowing in the first coil assembly 12 and the second coil assembly 14 is current free. Similarly, the first and second portions 14a, 14b of the second coil assembly 14 cooperate to generate a second stationary field free line 16b at a second location L2 when a current is flowing in the second coil assembly 14 and the first coil assembly 12 is current free. The second stationary field free line 16b is translated with respect to the first stationary field free line 16a along the propagation direction P.

To generate the traveling field free line 16, the first and second coil assemblies 12, 14 are connected to the controller 18 via controlling paths 18a, 18b, such as electrical control lines. The controller 18 controls the current amplitudes in the first and second coil assemblies 12, 14. Hence, by initializing the traveling field free line 16 at the first location L1 with the first coil assembly 12 and subsequently driving the first and second coil assemblies 12, 14 with corresponding driving currents synchronized with each other such that the amplitude of the first driving current in the first coil assembly 12 is decreasing and the amplitude of the second driving current in the second coil assembly 14 is increasing, the traveling field free line 16 may travel along the propagation direction P from the first location L1 to the second location L2.

The first and second coil assemblies 12, 14 define a through-going passage 20 through the first and second coil assemblies 12, 14 along the propagation direction P, such that the traveling field free line 16 travels substantially within the through-going passage 20 when the first and second coil assemblies 12, 14 are driven by the controller 18. Thus, a sample S introduced into the through-going passage 20 may be scanned with the traveling field free line 16.

An exemplary driving scheme for the system 10 includes first and second current amplitudes $A_1$ and $A_2$ corresponding to the current amplitudes in the first and second coil assemblies 12, 14, which are varied according to periodic functions with a characteristic drive frequency $\omega_1$. For example, a continues scanning of the sample S, such as from the first location L1 to the second location L2 may be achieved by varying the current amplitudes $A_1$, $A_2$ according to $$A_1 = a_1 \cos(\omega_1 t); \text{ and} \quad (1)$$

$$A_2 = a_2 \sin(\omega_1 t); \quad (2)$$

wherein t relates to time, and $a_1$, $a_2$ are proportionality constants. Then, at t=0, the first stationary field free line 16a is generated at the first location L1, while at t=π/2, the second stationary field free line 16b is generated at the second location L2 by the system 10, and at intermediate times 0>t>π/2, the traveling field free line 16 travels between the first location L1 and the second location L2.

Figure 2:
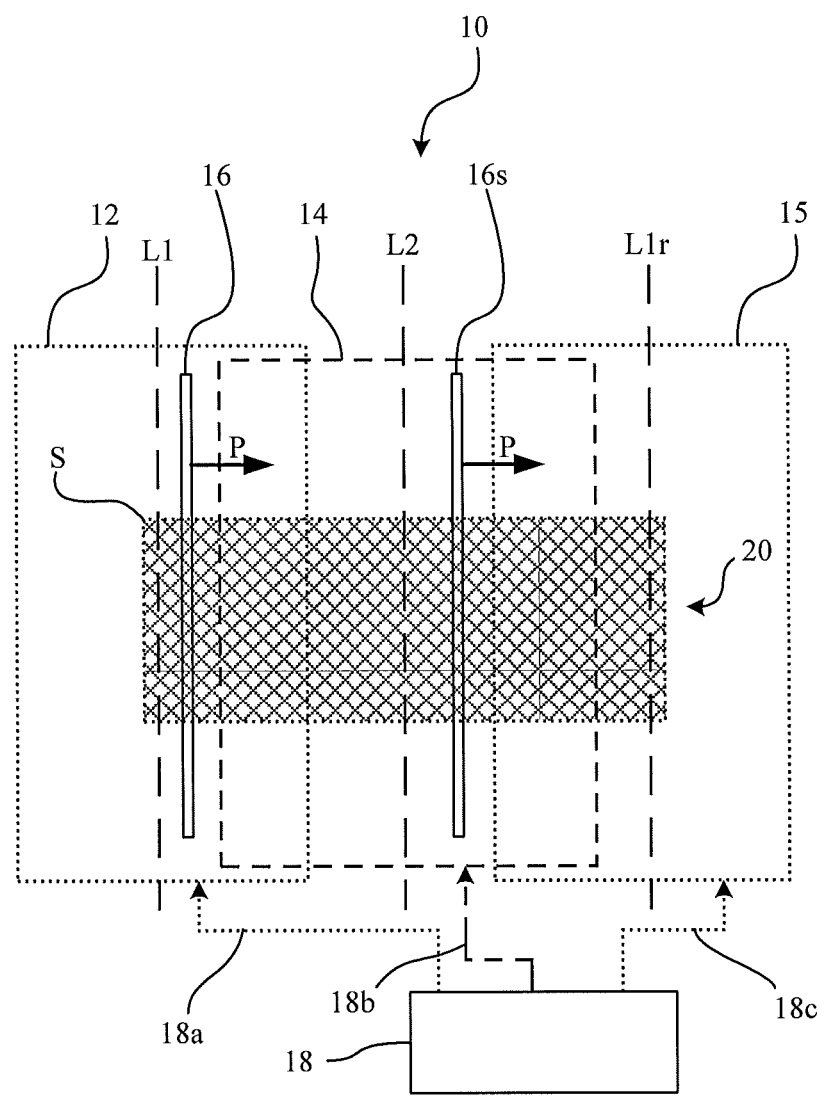
FIG. 2 is a schematic illustration of a system for generating two synchronized traveling field free lines in a probe volume according to an example.

FIG. 2 shows an embodiment of a system 10, wherein the traveling distance of the traveling field free line 16 along the propagation direction has been extended to increase the probe volume accessible by the system 10 along the propagation direction P. The system 10 comprises first and second coil assemblies 12, 14 partially overlapping with each other at a first end of the second coil assembly 14. The system 10 further comprises an additional coil assembly 15 overlapping with the second coil assembly 14 at a second end of the second coil assembly 14. The additional coil assembly 15 may be structurally equivalent to the first coil assembly 12 but translated along the propagation direction P.

Each of the first, second and additional coil assemblies 12, 14, 15 may be adapted for generating a stationary field free line 16a, 16b at respective stationary field free line locations L1, L2 and L1r, when a current is flowing in the respective coil assembly 12, 14, 15 and the other coil assemblies 12, 14, 15 are current free. The respective stationary field free line locations L1, L2 and L1r are distributed along the propagation direction P to provide well defined intermediate positions for the traveling field free line 16 traveling along the propagation direction P.

The controller 18 can control the driving current in the first, second and additional coil assemblies 12, 14, 15 such that the first and second coil assemblies 12, 14 cooperate to generate a traveling field free line 16 in accordance with the embodiment illustrated in FIG. 1 and the second and additional coil assemblies 14, 15 cooperate to generate a synchronized traveling field free line 16s. For example, the controller 18 may drive the first, second and additional coil assemblies 12, 14, 15 with the same periodic function being periodic in time with a periodicity of $2\pi$, the drive signals of the first, second and additional coil assemblies 12, 14, 15 having phase shifts between each other, such as a phase shift of $\pi/2$ between the driving signals of the first and second coil assemblies 12, 14 and a phase shift of $\pi/2$ between the driving signals of the second and additional coil assemblies 14, 15. Thus the two traveling field free lines 16, 16s may travel in the same direction along the propagation direction P, wherein the distance between the two traveling field free lines 16, 16s can be kept constant.

Naturally, by concatenating further additional coil assemblies 15 along the propagation direction P, an arbitrary length of the system 10 may be achieved along the propagation direction P.

Figure 3A:
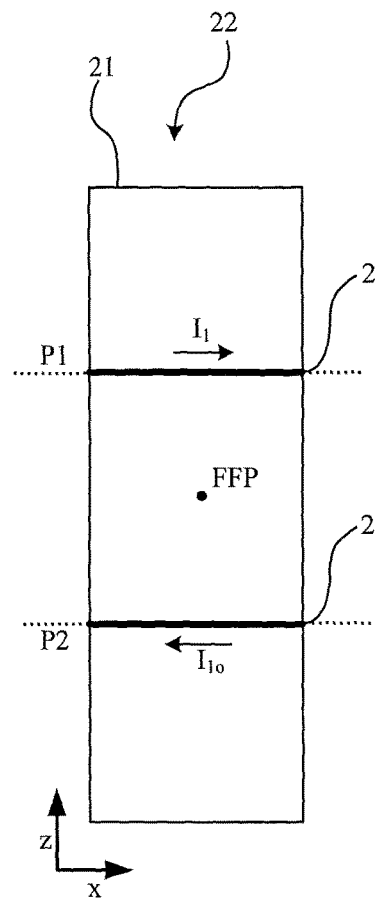
FIG. 3A is a schematic top view of a Maxwell coil assembly according to an example.
Figure 3B:
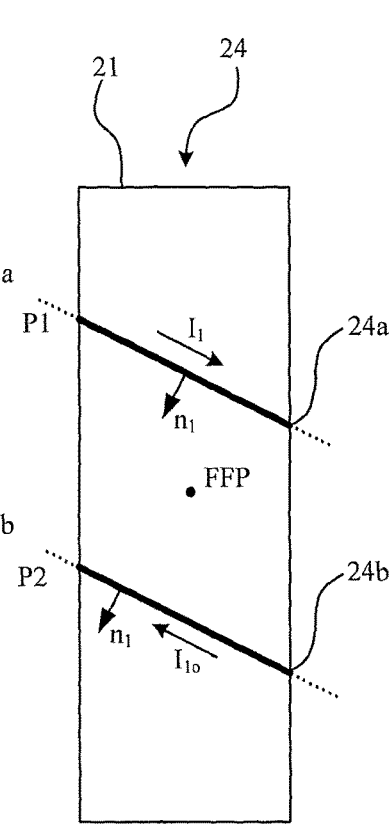
FIG. 3B is a schematic top view of a tilted Maxwell coil assembly according to an example.
Figure 3C:
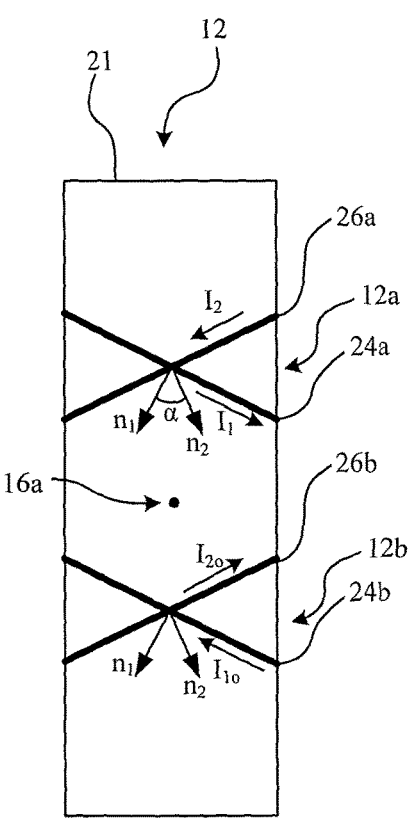
FIG. 3C is a schematic top view of two combined tilted Maxwell coil assemblies in a crossed coil configuration according to an example.

FIGS. 3A to 3C illustrate individual parts of an exemplary arrangement for the first or second coil assemblies 12, 14 for generating a stationary field free line 16a, 16b compatible with the system 10 illustrated in FIGS. 1 and 2.

FIG. 3A shows a top view of a Maxwell coil assembly 22 comprising a first coil 22a and a second coil 22b, arranged in respective parallel planes P1, P2 arranged along the horizontal direction (x-direction) and extending along the y-direction, i.e. into the plane of the drawing. The coils 22a, 22b are wound on a cylindrical coil carrier 21, the coil carrier 21 extending in the vertical direction (z-direction). The first and second coils 22a, 22b are configured to be driven by opposite driving currents $I_1$, $I_{10}$ such as to generate a magnetic field gradient in a space between the parallel planes P1, P2. Particularly, the Maxwell coil assembly 22 is expected to generate a field free point FFP at a middle location between the first and second coils 22a, 22b.

FIG. 3B shows a top view of a tilted Maxwell coil assembly 24 comprising a first coil 24a and a second coil 24b configured to be driven by opposite driving currents $I_1$, $I_{10}$ and to generate a magnetic field gradient between the parallel planes P1, P2. The tilted Maxwell coil assembly 24 differs from the Maxwell coil assembly 22 in that the coils 24a, 24b of the tilted Maxwell coil assembly 24 are tilted with respect to the longitudinal direction of the cylindrical coil carrier 21 (z-direction in the drawing). In some embodiments, the first and second coils 24a, 24b are identical or mirrored coils. $n_1$, $n_2$ are normal directions of the respective planes P1, P2, which the coils 24a, 24b lie in.

Similar to the Maxwell coil assembly 22, the tilted Maxwell coil assembly 24 is expected to produce a field free point FFP at a middle location between the first and second coils 24a, 24b.

However, a first stationary field free line 16a may be generated by a combination of a first tilted Maxwell coil assembly 24 and a second tilted Maxwell coil assembly 26 constituting a first coil assembly 12 as illustrated in FIG. 3C.

In FIG. 3C, the first stationary line 16a extends along the y-direction and perpendicular to the paper plane.

The first and second tilted Maxwell coil assemblies 24, 26 are similar to the tilted Maxwell coil assembly 24 illustrated in FIG. 3B, but have opposite tilt angles with respect to the longitudinal direction of the cylindrical coil carrier 21. In other words, the normals $n_1$, $n_2$ of the parallel planes P1, P2, which the coils 24a, 24b, 26a, 26b of the first and second tilted Maxwell coil assemblies 24, 26 lie in, form a nonzero angle $\alpha$.

The first tilted Maxwell coil assembly 24 comprises the first and second coils 24a, 24b which can be driven by opposite driving currents $I_1$, $I_{10}$. The second tilted Maxwell coil assembly 26 comprises the first and second coils 26a, 26b which can be driven by opposite driving currents $I_2$, $I_{20}$.

As shown in FIG. 3C, the respective first coils 24a, 26a and the respective second coils 24b, 26b overlap to form respective first and second pairs of crossed coils 12a, 12b as exemplary first and second portions 12a, 12b of the first coil assembly 12 shown in FIG. 1.

When both the first and second Maxwell coil assemblies 24, 26 are driven with driving currents $I_1$, $I_2$, a first stationary field free line 16a at a middle location L1 between the first and second pairs of crossed coils 12a, 12b may be generated, said first stationary field free line 16a extending along the y-direction.

Figure 4A:
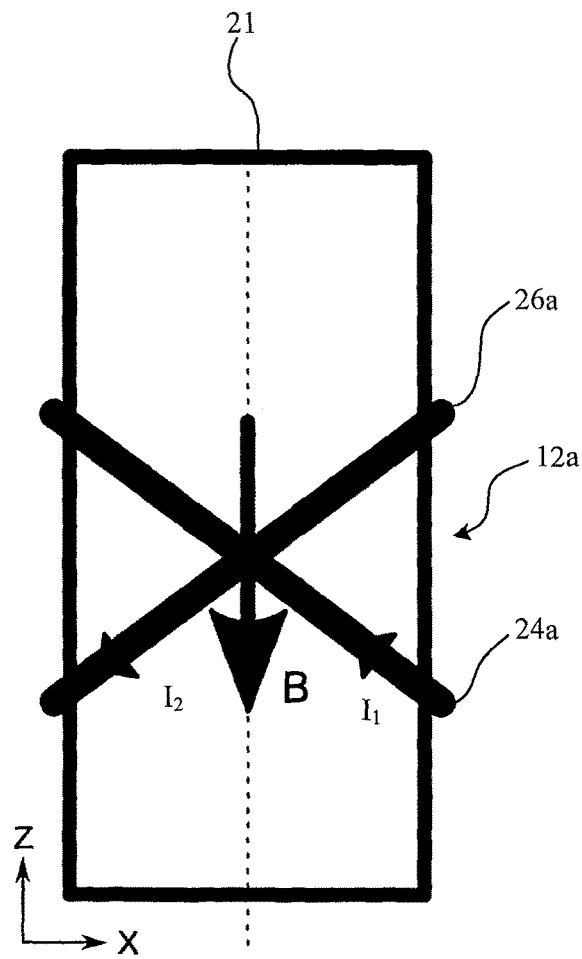
FIG. 4A is a schematic illustration of the magnetic field generated by a pair of crossed coils according to an example.
Figure 4B:
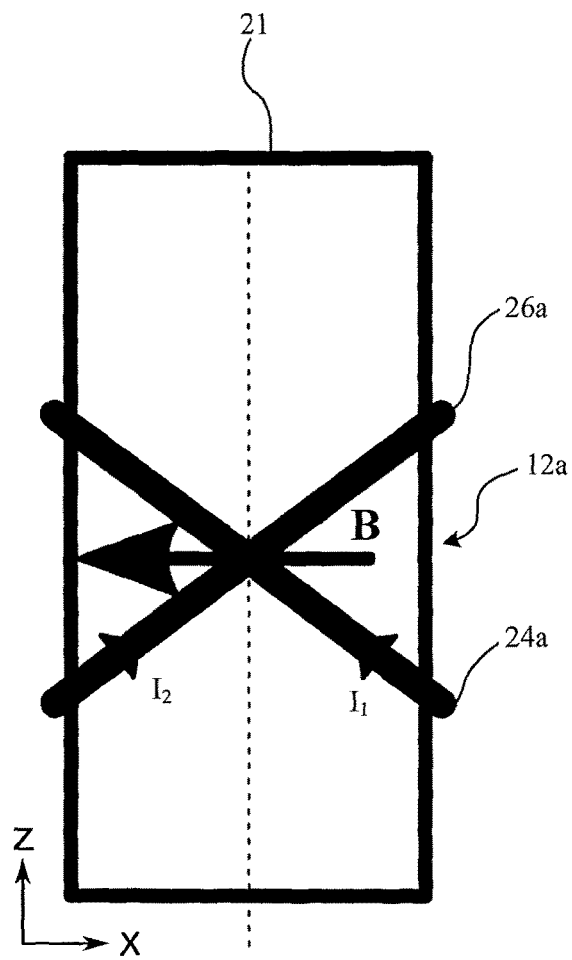
FIG. 4B is a schematic illustration of the magnetic field generated by a pair of crossed coils according to another example.

FIGS. 4A, 4B illustrates two possibilities for the respective driving current configurations exemplarily shown in a top view of a first pair of crossed coils 12a of a first coil assembly 12.

FIG. 4A shows a first configuration, wherein currents $I_1$, $I_2$ are driven in the first pair of crossed coils 12a, such that at a middle location of the pair of crossed coils 12a, the magnetic field B is oriented along the longitudinal direction of the coil carrier 21 and thereby substantially points in the direction of the second pair of crossed coils 12b (not shown).

FIG. 4B shows a preferred second configuration, wherein currents $I_1$, $I_2$ are driven in the first pair of crossed coils 12a, such that at a middle location of the first pair of crossed coils 12a, the magnetic field B is oriented transverse with respect to the z-direction, i.e. the longitudinal direction of the coil carrier 21. In other words, the first and second pairs of crossed coils 12a, 12b may be spaced apart along a separation direction, while the magnetic fields generated individually by said first and second pairs of crossed coils 12a, 12b driven by driving currents according to the second configuration form a nonzero angle with said separation direction, in particular an angle deviating from 90° by less than 30°, preferably by less than 10°.

Figure 5:
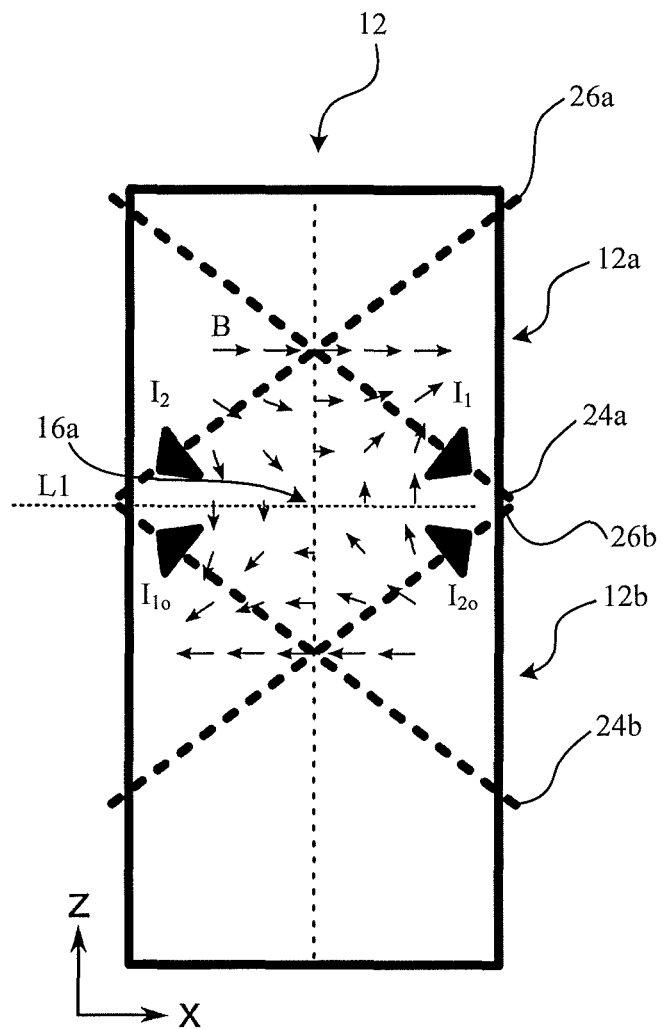
FIG. 5 is a schematic illustration of two tilted Maxwell coil assemblies in a crossed coil configuration and the associated magnetic field distribution according to an example.

FIG. 5 illustrates the magnetic field profile generated by first and second pairs of crossed coils 12a, 12b in the second configuration in a central plane going through a middle location of the first coil assembly 12 when viewed along the y-direction, such that the first and second tilted Maxwell coil assemblies 24, 26 form a cross-shape. In other words, the y-direction may be aligned with the crossing direction determined from the vector cross product of the normals $n_1$, $n_2$ of the parallel planes P1, P2 of the first and second tilted Maxwell coil assemblies 24, 26, i.e. along the intersection line of the parallel planes P1, P2 associated with the pairs of crossed coils 12a, 12b.

The pairs of crossed coils 12a, 12b are depicted with dashed lines, the current direction in the respective courts being indicated by triangle-shaped solid arrow heads on the dashed lines. The magnetic field directions at exemplary points are illustrated with straight black arrows, such as the black arrow close to the reference sign B.

As the currents in oppositely arranged coils 24a, 24b and 26a, 26b of the first and second tilted Maxwell coil assemblies 24, 26, which are forming the two pairs of crossed coils 12a, 12b, are flowing in opposite directions, the magnetic fields generated by the first and second pairs of crossed coils 12a, 12b at their respective middle locations should point in opposite directions.

However, in a middle location L1 of the first coil assembly 12 between the first and second pairs of crossed coils 12a, 12b, the respective magnetic field contribution of the first and second pairs of crossed coils 12a, 12b can cancel along the y-direction, such that a first stationary field free line 16a can be formed at said middle location L1.

At a vertical position along the z-direction corresponding to the location L1 of the first stationary field free line 16a, the magnetic field B may substantially point along the z-direction and may reverse sign along the x-direction.

Far from the vertical position along the z-direction corresponding to the location L1 of the first stationary field free line 16a, the magnetic field B may substantially point along the x-direction and may reverse sign along the z-direction.

Thus, the position of the field free line 16a may be translated along the z-direction by applying a magnetic field along the x-direction, while it may be translated along the x-direction by superposing a magnetic field applied along the z-direction.

At the same time, the first coil assembly 12 defines a through-going passage 20 oriented along the z-direction and adapted to introduce a sample S to be investigated into the coil carrier 21. Using a first coil assembly 12 with these properties, a system 10 for generating a traveling field free line 16, the traveling field free line 16 traveling along the z-direction and translatable radially along the x-direction with a magnetic field applied along the z-direction, can be constructed as will be described with reference to FIGS. 6A to 6D.

FIGS. 6A to 6D illustrate a combination of a first and second coil assembly 12, 14 to form a system 10 for generating a traveling field free line 16. The upper portions of the figures show the coil assemblies 12, 14 when viewed along the y-direction, the y-direction corresponding to the orientation of the traveling field free line 16, while the lower portions of the figures show the coil assemblies 12, 14 when viewed along z-direction, the z-direction corresponding to the propagation direction P of the traveling field free line 16 to be generated by the system 10. In the illustrated embodiments, both the first and second coil assemblies 12, 14 comprise first and second tilted Maxwell coil assemblies 24, 26 with a driving current configuration equivalent to the second configuration illustrated in FIG. 4B.

FIG. 6A shows the arrangement of a first coil assembly 12 on a coil carrier 21 to generate a first stationary field free line 16a at a first location L1.

FIG. 6B shows a second coil assembly 14 on the same coil carrier 21, the second coil assembly 14 being identical to the first coil assembly 12, but displaced along the z-direction by half the extension L of the first pair of crossed coils 12a of the first coil assembly 12 along the z-direction to generate a second stationary field free line 16b at a second location L2 translated by L/2 along the z-direction with respect to the first location L1.

FIG. 6C shows both the first coil assembly 12 and the second coil assembly 14 arranged on the same coil carrier 21, wherein the positions of the first and second coil assemblies 12, 14 on the common coil carrier 21 are identical to the positions illustrated in FIGS. 6A, 6B.

When driving the first and second coil assemblies 12, 14 with corresponding driving currents synchronized with each other, a traveling field free line 16 may be generated and translated along the z-direction according to a traveling path 28 to scan a two-dimensional plane going through the first and second stationary field free lines 16a, 16b. In particular, superposing the magnetic field contributions of the translated first and second coil assemblies 12, 14, field free lines 16 at intermediate positions along said two-dimensional plane can be generated.

Hence, a traveling field free line 16 may be generated in the through-going passage 20 through the coil carrier 21.

FIG. 6D shows the same system 10 as in FIG. 6C but with an additional deflection coil assembly 30 implemented by a solenoid wound around the coil carrier 21 and extending along the z-direction, such as to generate a magnetic field along the z-direction. The coil assemblies 12, 14 are schematically depicted using dashed lines to increase the visibility of the traveling path 28 of the traveling field free line 16 in the figure.

As described above with reference to FIG. 5, at the vertical position along the z-direction corresponding to the position of the traveling field free line 16, the magnetic field is mostly oriented along the z-direction and reverses sign along the x-direction. Hence, by applying a magnetic field along the z-direction with the deflection coil assembly 30, the traveling field free line 16 may be deflected along a deflection direction D, the deflection direction D corresponding substantially to the x-direction in the illustrated example.

Thus, by generating a traveling field free line 16 with the first and second coil assemblies 12, 14 and modulating the current in the deflection coil assembly 30, a meandering traveling path 28 may be imposed on the traveling field free line 16, such as to scan a two-dimensional surface spanned by the z- and x-directions with the traveling field free line 16 as illustrated in FIG. 6D.

Figure 7:
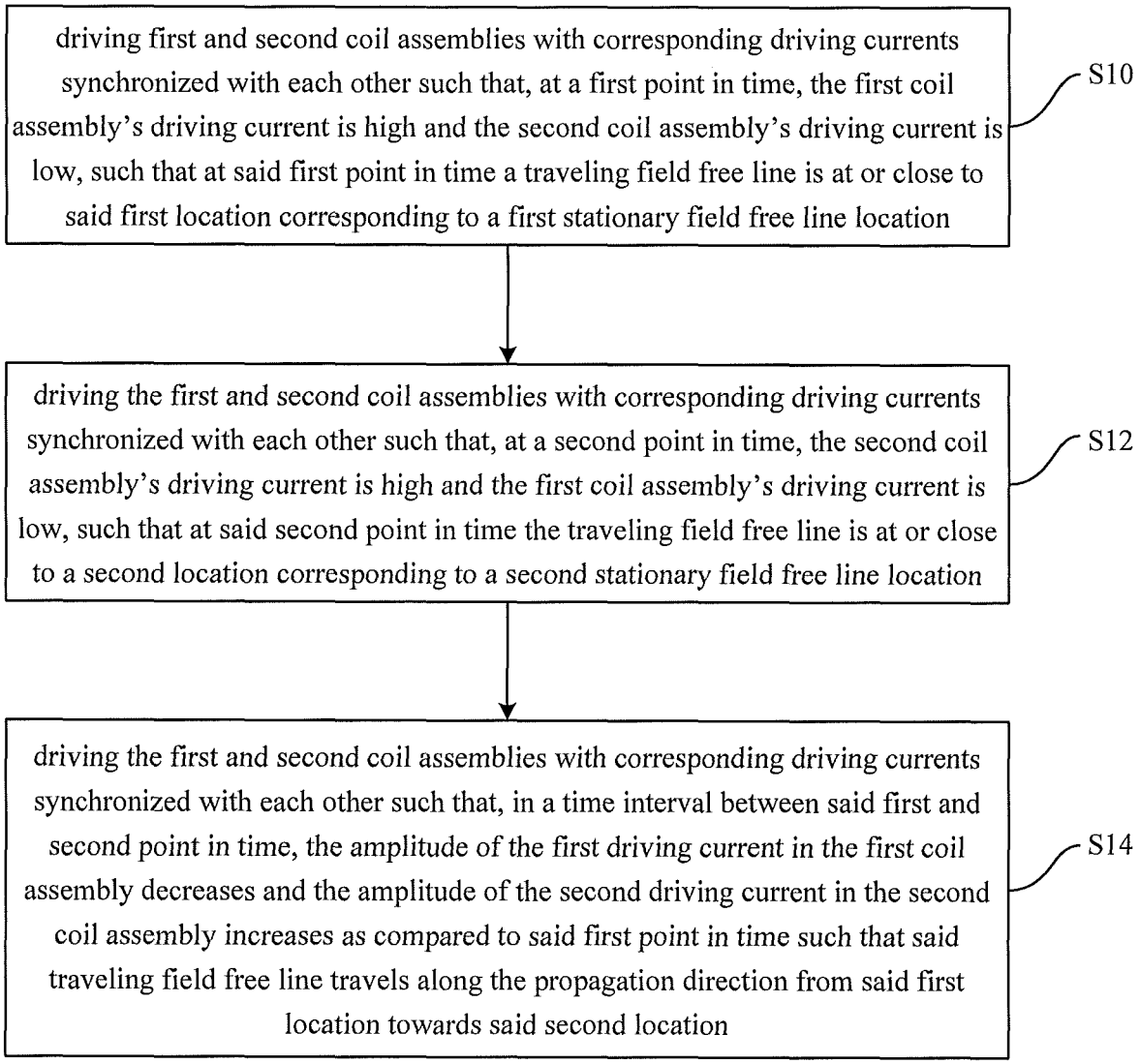
FIG. 7 is a flowchart of a method for generating a traveling field free line according to an example.

A flowchart of a method for generating a traveling field free line 16 is illustrated in FIG. 7. The first coil assembly is configured for generating a first stationary field free line at a first location when a current is flowing in the first coil assembly and the second coil assembly is current free. The second coil assembly is configured for generating a second stationary field free line at a second location, when a current is flowing in the second coil assembly and the first coil assembly is current free. The method comprises driving the first and second coil assemblies with corresponding driving currents synchronized with each other such that at a first point in time, the first coil assembly's driving current is high and the second coil assembly's driving current is low, such that at said first point in time the traveling field free line is at or close to said first location (step S10), and a second point in time, the second coil assembly's driving current is high and the first coil assembly's driving current is low, such that at said second point in time the traveling field free line is at or close to said second location (step S12), and in a time interval between said first and second point in time, the amplitude of the first driving current in the first coil assembly decreases and the amplitude of the second driving current in the second coil assembly increases as compared to said first point in time such that said traveling field free line travels along the propagation direction from said first location towards said second location (step S14).

By implementing said method in one of the systems 10 described above, a traveling field free line 16 traveling along the propagation direction P between said first location L1 and said second location L2 may be generated. In particular, an investigated sample S may scanned along the propagation direction with the traveling field free line 16 such that magnetizable particles in the sample S can have their magnetization direction reversed or substantially reversed by or during the passage of the magnetic field free line 16, such that a magnetic signal characteristic for a magnetization reversal of said magnetizable particles, which is measured in or close to the system 10 can be attributed towards the current location of the traveling field free line 16.

Figure 8A:
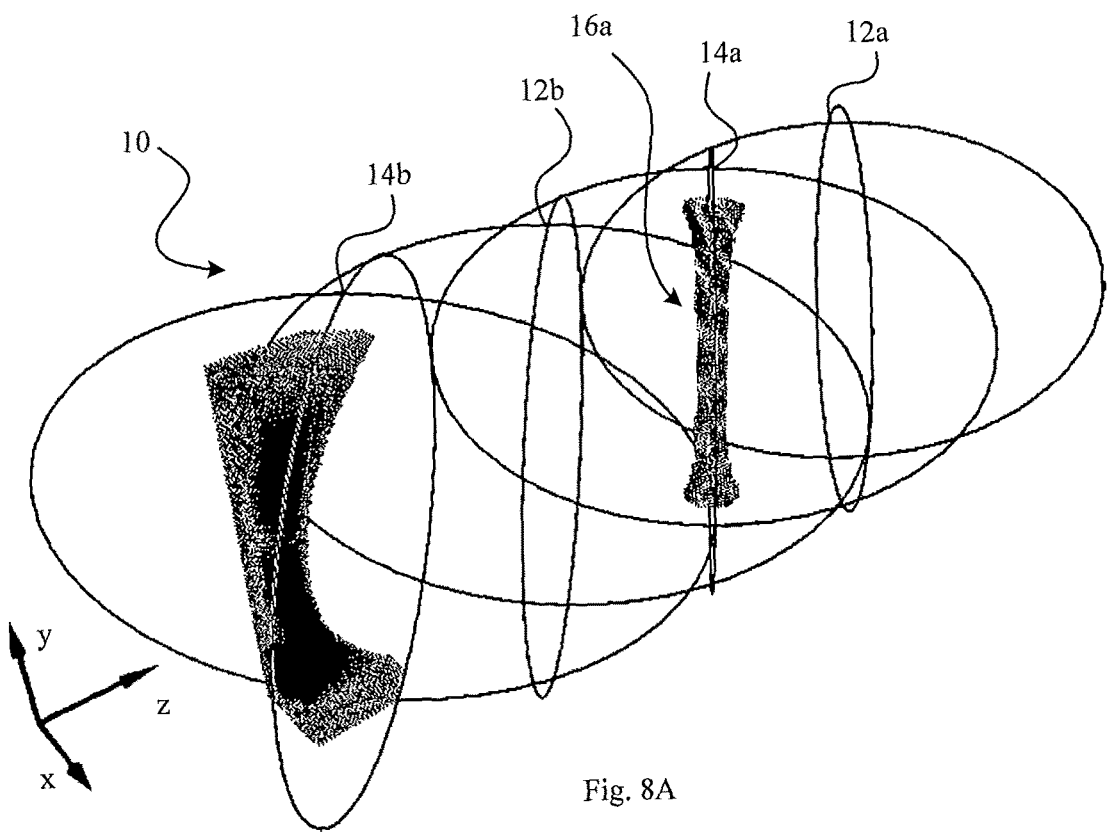
FIG. 8A is a simulation of the location of a field free line in a system for generating a traveling field free line according to an example.
Figure 8B:
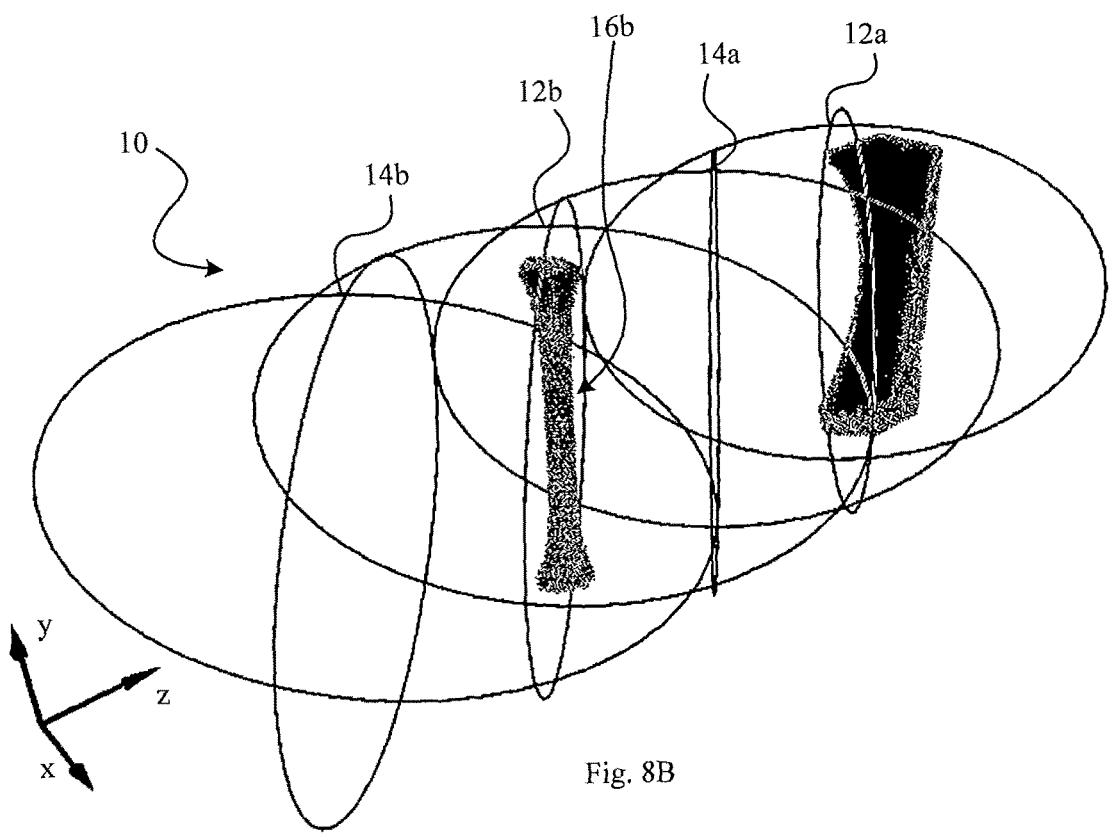
FIG. 8B is a simulation of the location of a field free line in a system for generating a traveling field free line according to another example.

A simulation of the position of the first and second stationary field free lines 16a, 16b is illustrated in FIGS. 8A and 8B, respectively, simulated in an exemplary system 10 for generating a traveling field free line 16 comprising first and second coil assemblies 12, 14, wherein each of the first and second coil assemblies 12, 14 comprise two first and second tilted Maxwell coil assemblies 24, 26 in a crossed coil configuration. In the illustrated simulation, regions having close to zero magnetic fields appear darkened.

FIG. 8A illustrates a situation, in which the first and second pairs of crossed coils 12a, 12b of the first coil assembly 12 are driven with a current as explained in detail with reference to FIG. 5, while the second coil assembly 14 is mostly current free. The first stationary field free line 16a can be identified by the column-shaped black region located at a middle location between the first and second pairs of crossed coils 12a, 12b of the first coil assembly 12.

FIG. 8B illustrates the opposite situation, in which the first and second pairs of crossed coils 14a, 14b of the second coil assembly 14 are driven with a current as explained in detail with reference to FIG. 5, while the first coil assembly 12 is mostly current free. Analogous to the situation illustrated in FIG. 8A, the second stationary field free line 16b can be identified by the column-shaped black region located at a middle location between the first and second pairs of crossed coils 14a, 14b of the second coil assembly 14.

As can be seen from FIG. 8B, when the traveling field free line 16 is formed at the location of the second stationary field free line 16b, at an edge of the system 10 close to the first pair of crossed coils 12a, a field free region forms. When the traveling field free line 16 travels past the position of the second stationary field free line 16b, it can leave the system 10, during which the traveling field free line 16 disperses at a position close to the second pair of crossed coils 14b of the second coil assembly 14, while a new traveling field free line 16 forms close to the first pair of crossed coils 12a of the first coil assembly 12. Hence, by modulating the current amplitude in the first coil assembly 12 and in the second coil assembly 14 with a periodic function, wherein the current amplitudes in the first coil assembly 12 and the current amplitudes in the second coil assembly 14 are associated with a relative phase shift, such as π/2, a continuous train of traveling field free lines 16 continuously traveling from the first pair of crossed coils 12a of the first coil assembly 12 towards the second pair of crossed coils 14b of the second coil assembly 14 can be generated.

Using a deflection coil assembly 30 to deflect the traveling field free line 16 along a deflection direction which is different from the propagation direction P, a three-dimensional probe volume may be scanned with the traveling field free line 16 as previously described with reference to FIG. 6D. However, to attribute a three-dimensional coordinate of the magnetizable particles in the sample S, the sample S should be scanned with more than one orientation of the traveling field free line 16 analogous to computer tomography imaging schemes.

A different orientation of the traveling field free line 16 may be provided by a third and a fourth coil assembly, the third and fourth coil assemblies being adapted for generating third or fourth stationary field free lines, when a current is flowing in the third or fourth coil assemblies, respectively, while the other coil assemblies are current free. Particularly, the third and fourth stationary field free lines should have different orientations than the first and second stationary field free lines 16a, 16b.

Figure 9A:
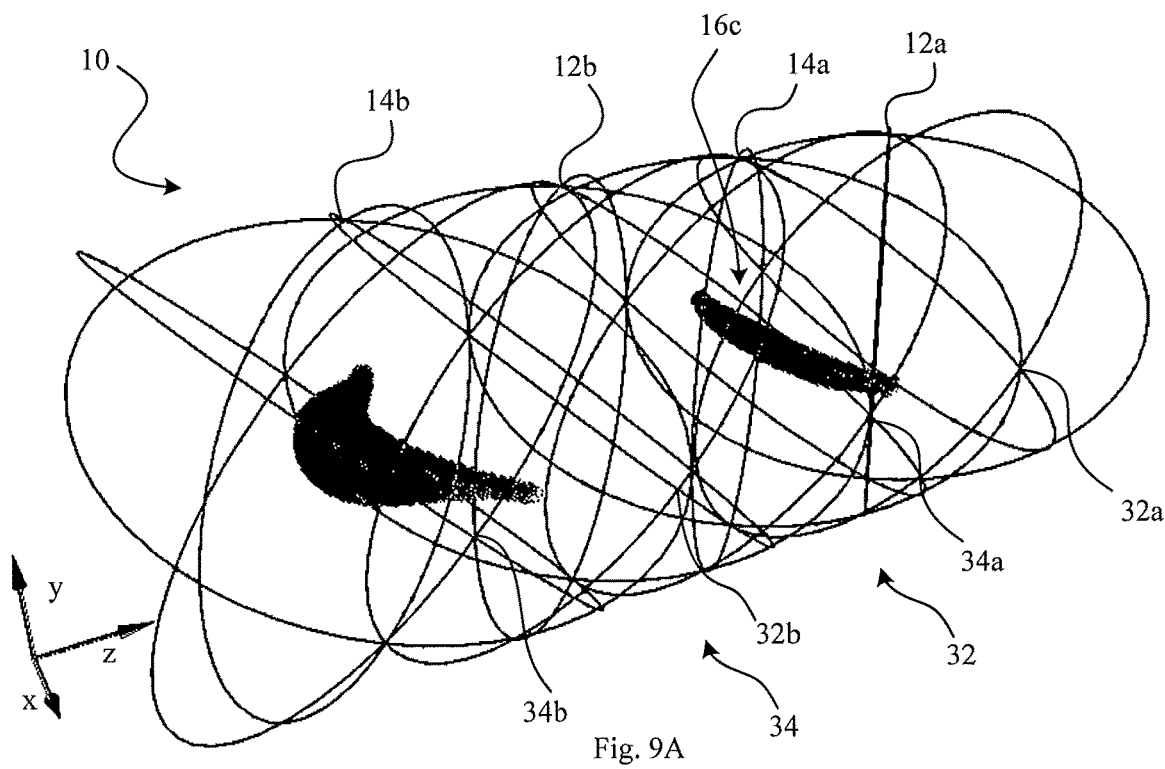
FIG. 9A is a simulation of the location of a field free line in a system for generating a traveling field free line according to another example.
Figure 9B:
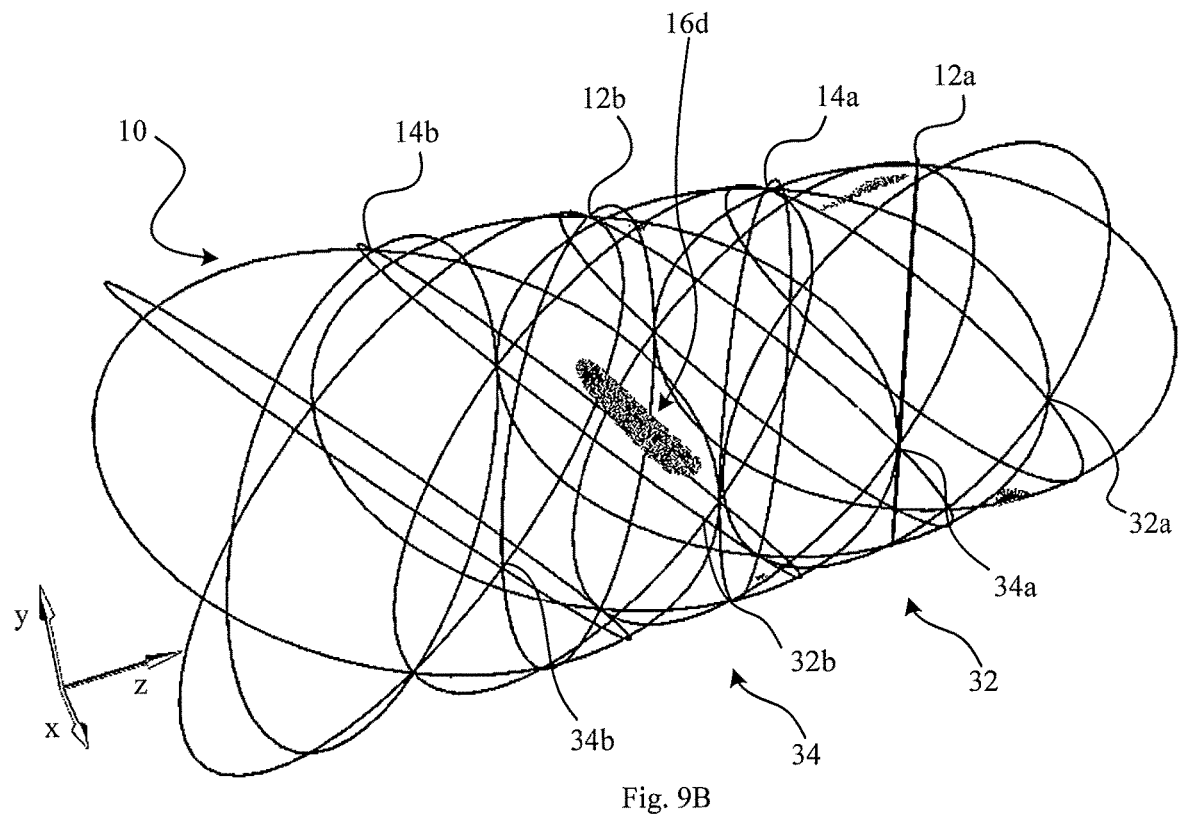
FIG. 9B is a simulation of the location of a field free line in a system for generating a traveling field free line according to another example.

FIGS. 9A and 9B show a system 10 having both first and second coil assemblies 12, 14, as well as third and fourth coil assemblies 32, 34, having similar coil configurations as in FIGS. 8A and 8B. The illustrated third and fourth coil assemblies 32, 34 are identical to the first and second coil assemblies 12, 14, but are rotated about the z-direction by an angle of 90°. The third coil assembly 32 comprises first and second pairs of crossed coils 32a, 32b, and the fourth coil assembly 34 comprises first and second pairs of crossed coils 34a, 34b.

FIG. 9A illustrates a situation, in which the third and fourth pairs of crossed coils 32a, 32b of the third coil assembly 32 are driven with a current as explained in detail with reference to FIG. 5, while the first, second and fourth coil assembly 34 are mostly current free. The third stationary field free line 16c can be identified by the column-shaped black region located at a middle location between the first and second pairs of crossed coils 32a, 32b of the third coil assembly 32.

FIG. 9B illustrates the opposite situation, in which the third and fourth pairs of crossed coils 34a, 34b of the fourth coil assembly 34 are driven with a current as explained in detail with reference to FIG. 5, while the first, second and third coil assembly 32 are mostly current free. Analogous to the situation illustrated in FIG. 8A, the fourth stationary field free line 16d can be identified by the column-shaped black region located at a middle location between the first and second pairs of crossed coils 34a, 34b of the fourth coil assembly 34.

Thus, by combining the first through fourth coil assemblies 12, 14, 32, 34, a traveling field free line 16 having arbitrary orientation within a plane defined by the x- and y-directions and at a desired position along the propagation direction P oriented along the z-direction of the illustrated system 10 may be generated within the open bore defined by the first through fourth coil assemblies 12, 14, 32, 34.

FIGS. 10A to 10C illustrate a coil carrier 21 according to different perspective views, the coil carrier 21 being specifically adapted for holding a first and a third coil assembly 12, 32 each comprising two tilted Maxwell coil assemblies 24, 26, such as to generate a stationary field free line 16a-16d having an arbitrary orientation. Particularly, a dense wiring may be achieved by sharing a common coil wire between coils of the respective pairs of crossed coils 12a, 12b, 14a, 14b, 32a, 32b, 34a, 34b.

The illustrated embodiment features a roughly cylindrical shape of the coil carrier 21 defining a through-going passage 20 through the interior of the cylindrical coil carrier 21 and a cylindrical outer surface 35 for holding windings of coil wire. The coil carrier 21 further features anchoring points 36a to 36f and anchoring points 38a to 38f (only anchoring points 38a to 38c are visible in the figures) for providing anchoring locations for the coil wire. As the skilled person will appreciate, the anchoring "points" are not points in a mathematical sense but rather relate to locations where the coil wire may be anchored.

Figure 11:
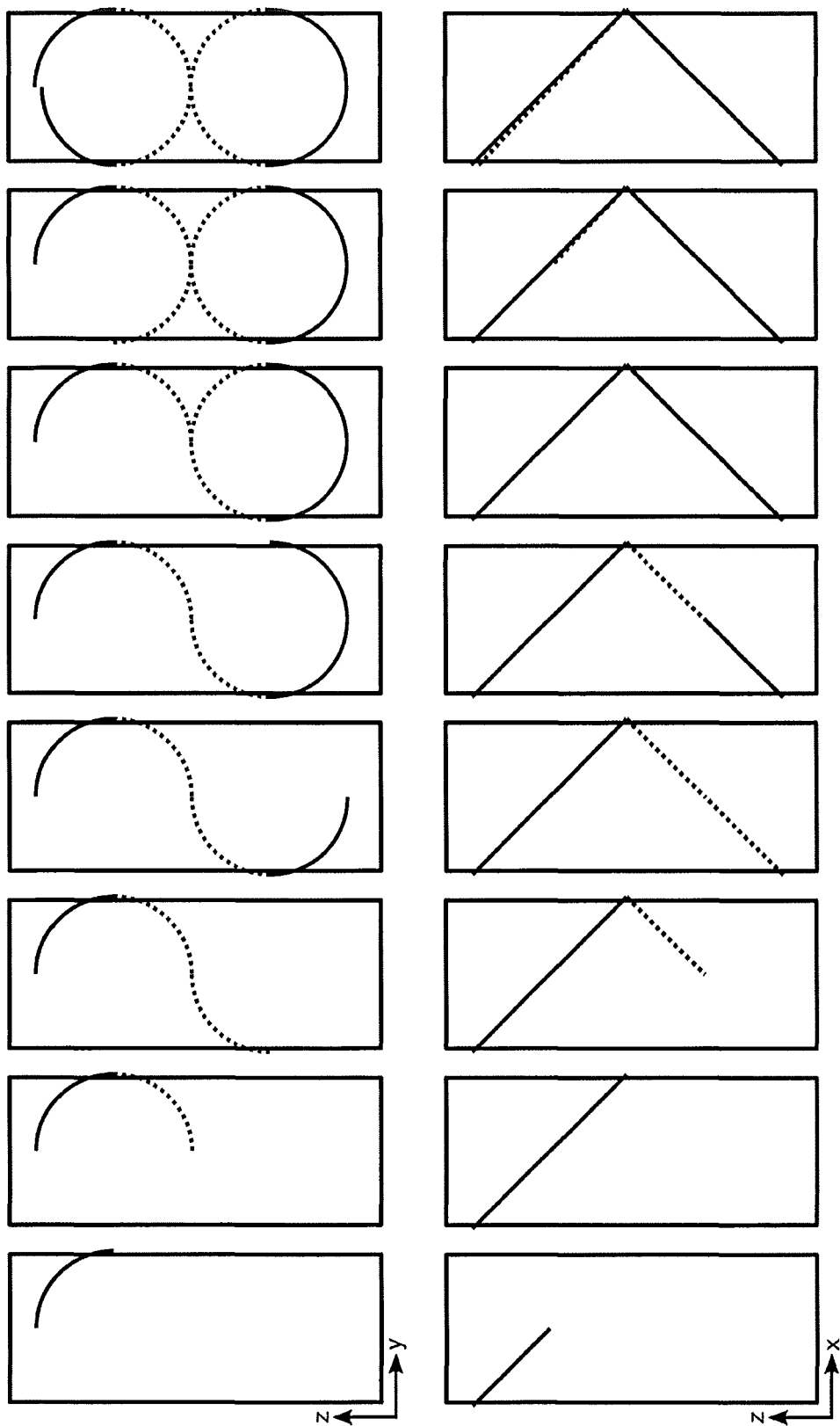
FIG. 11 illustrates a winding scheme of one half of an exemplary first coil assembly for use with a cylindrical coil carrier coil carrier according to an example.

A first illustrative step for a coil wire winding scheme, suitable for the coil carrier 21 illustrated in FIGS. 10A to 10C is illustrated in FIG. 11 by a series of intermediate steps of the winding scheme progressing from left to right. The upper row of intermediate steps shows a coil carrier 21 according to a side view, while the lower row of steps shows a coil carrier 21 according to a top view. Dashed portions of coil wire indicate windings on the back-side of the coil carrier 21 with respect to the illustrated perspective.

Applying said coil windings scheme of FIG. 11 to the coil carrier 21 illustrated in FIGS. 10A to 10C, making reference to the perspective view shown in FIG. 10A, a coil wire can be initially attached to an anchoring point 36a on the left side of the coil carrier 21. From said initial anchoring point 36a, the coil wire can be subsequently wound across the cylindrical outer surface 35 towards an oppositely arranged anchoring point 36e, which is located at a middle location of the coil carrier 21 arranged at an opposite side of the coil carrier 21 with respect to the anchoring point 36a. From said anchoring point 36e at said oppositely arranged middle location, the coil wire may be wound along the back-side (with respect to the perspective view illustrated in FIG. 10A) of the cylindrical outer surface 35 towards the anchoring point 36c at a right side of the cylindrical coil carrier 21. From said anchoring point 36c at the right side of the coil carrier 21, the coil wire can be wound around the cylindrical outer surface 35 of the coil carrier 21 via the anchoring point 36e towards the anchoring point 36a, such as to form two closed loops of the coil wire.

The two loops each define a respective plane P1, P2, the respective plane defining a normal $n_1$, $n_2$ direction of each closed loop. By repeating the process, two connected coils, whose normal $n_1$, $n_2$ directions are forming an angle $\alpha$, can be wound on to the coil carrier 21.

Winding a coil wire around the outer surface 35 starting from the anchoring point 36d and winding a coil wire around the coil carrier 21 from the anchoring point 36d via the anchoring point 36b towards the anchoring point 36f and back towards the anchoring point 36d via the anchoring point 36b allows forming two additional closed loops, the additional closed loops forming two pairs of crossed coils 12a, 12b, 14a, 14b with the two closed loops wound via the anchoring points 36a, 36e, 36c. Hence, a first coil assembly 12 can be wound onto the coil carrier 21 using the anchoring points 36a to 36f.

The above described winding scheme can be straightforwardly applied to the anchoring points 38a to 38f to wind a third coil assembly 32 onto the coil carrier 21.

A second and fourth coil assembly 14, 34 can be wound onto the same or a similar coil carrier 21, following the same winding scheme, particularly using a coil carrier 21 having a different diameter. For example, by inserting a coil carrier 21 having wound thereon a first and a third coil assembly 12, 32 into a coil carrier 21 having wound thereon a second and fourth coil assembly 14, 34, a system 10 for generating a traveling field free line 16 can be assembled, as long as the first and second as well as the third and fourth stationary field free lines 16a-16d corresponding to the first through fourth coil assemblies 12, 14, 32, 34 are translated with respect to each other along the axial direction of the cylindrical coil carriers 21.

Figure 12:
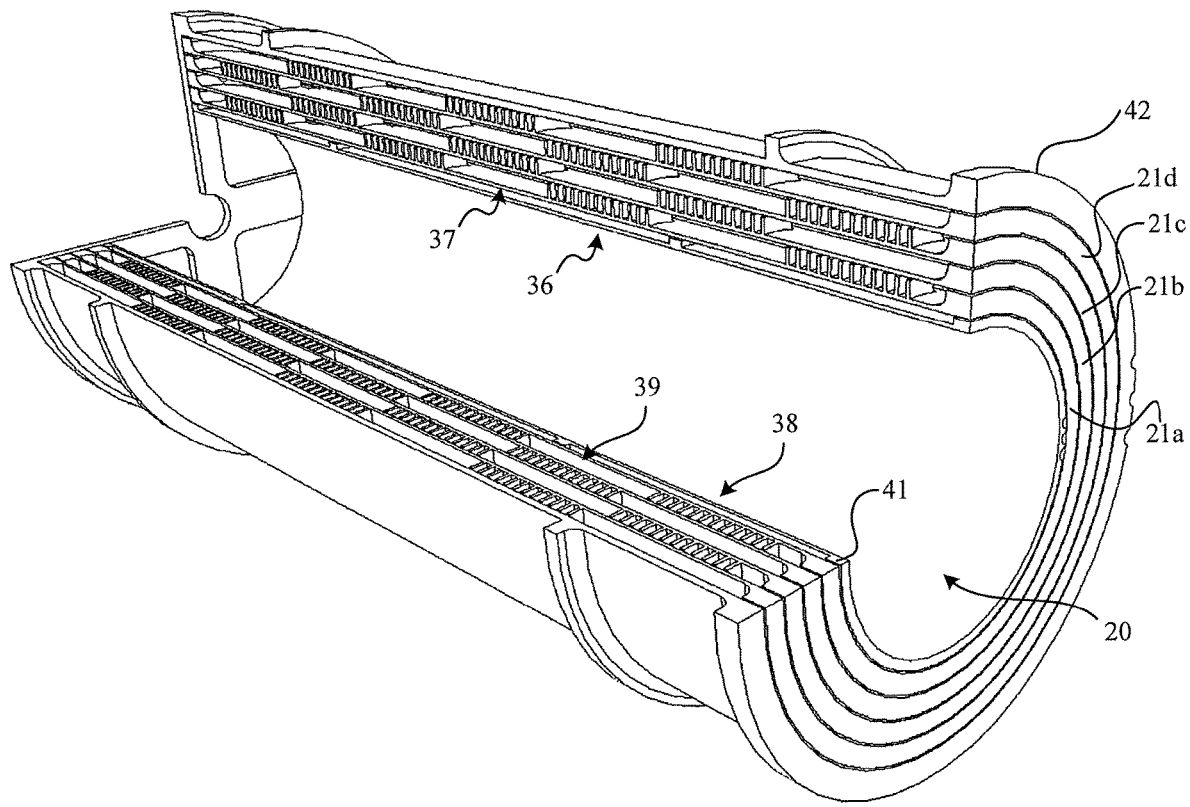
FIG. 12 illustrates a coil carrier assembly according to an example.

FIG. 12 shows a stacked coil carrier assembly 40 comprising stacked coil carriers 21a to 21d, wherein coil carriers 21a and 21c provide anchoring points 36, 38 for winding thereon first and third coil assemblies 12, 32, while coil carriers 21b and 21d provide anchoring points 37, 39 for winding thereon second and fourth coil assemblies 14, 34.

The stacked coil carrier assembly 40 further comprises coil carriers 41, 42 for winding thereon a measurement coil assembly and a deflection coil assembly 30, respectively. Hence, a dense assembly of coil wires defining first through fourth coil assemblies 12, 14, 32, 34 and matching deflection 30 and measurement coils can be provided. The stacked coil carrier assembly 40 defines a body of the system 10 having a through-going passage 20 defined by an open bore in the innermost cylindrical coil carrier 41 to accommodate an investigated sample S to be scanned with the traveling field free line 16.

Figure 13:
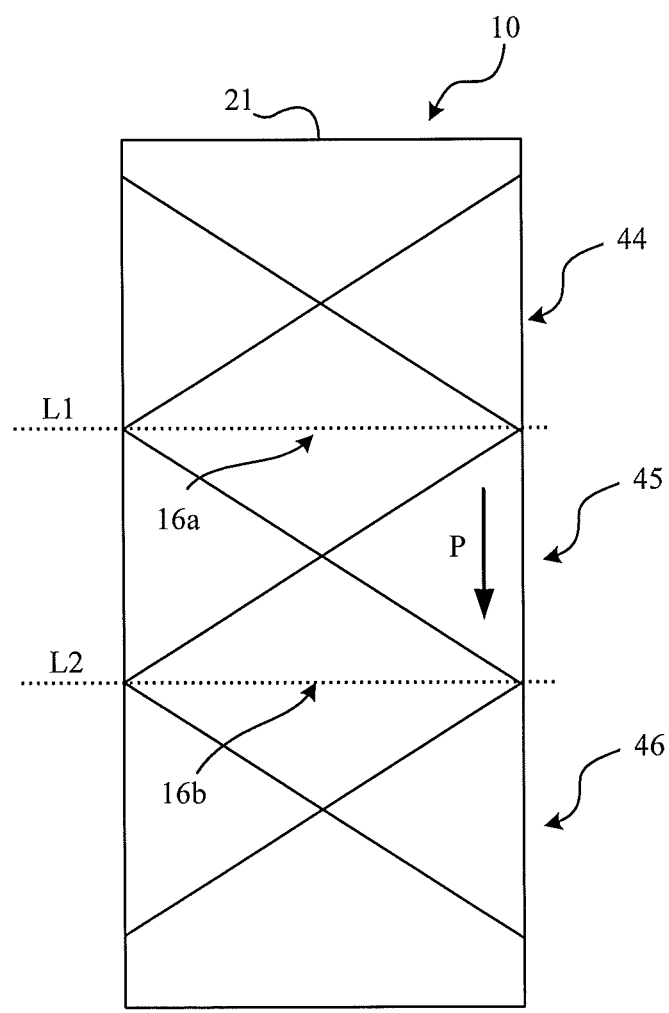
FIG. 13 illustrates a system for generating a traveling field free line, wherein first and second coil assemblies share a common coil portion according to an example.

FIG. 13 shows another embodiment of the system 10, wherein the first and second coil assemblies 12, 14 are formed by first through third crossed coils 44, 45, 46. The first coil assembly 12 comprises the first and second crossed coils 44, 45 and the second coil assembly 14 comprises the second and third crossed coils 45, 46. Hence, the second crossed coils 45 are shared between the first and second coil assemblies 12, 14.

Driving the first and second crossed coils 44, 45 as described with reference to FIG. 5, a first stationary field free line 16a may be generated at a middle location L1 between the first and second crossed coils 44, 45. Similarly, driving the second and third crossed coils 45, 46 as described with reference to FIG. 5, a second stationary field free line 16b may be generated at a middle location L2 between the second and third crossed coils 45, 46. Hence, by driving the first through third crossed coils 44, 45, 46 with synchronized drive currents, a traveling field free line 16 may be generated, the traveling field free line 16 traveling through the first and second stationary field free lines 16a, 16b.

Figure 14:
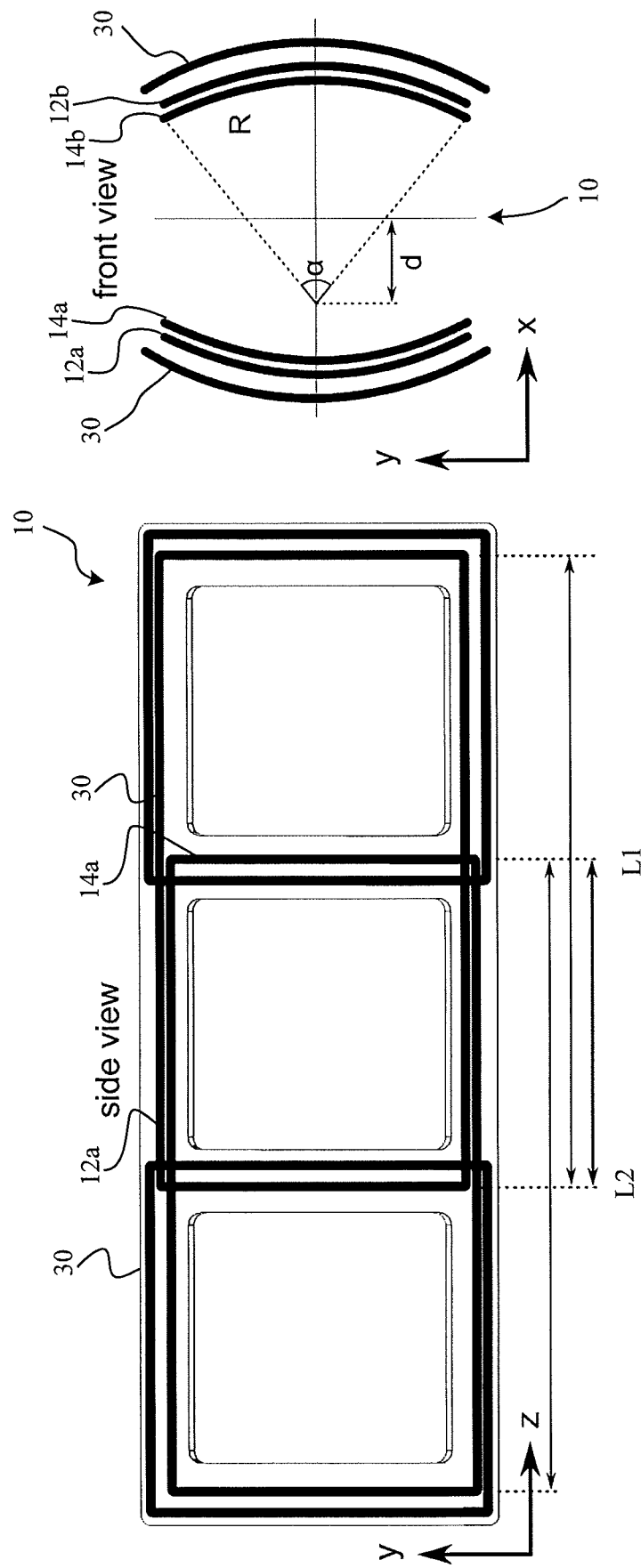
FIG. 14 illustrates an open system for generating a traveling field free line according to an example.

A further embodiment of an open system 10 for generating a traveling field free line 16 is illustrated in FIG. 14 showing a side view and front view of the system 10. The system 10 comprises a first and the second coil assembly 12, 14 to generate a traveling field free line 16, the traveling field free line 16 extending along the y-direction and traveling along the z-direction, and a deflection coil assembly 30 to translate the traveling field free line 16 along the x-direction.

Each of the first and second coil assemblies 12, 14 comprises oppositely arranged substantially rectangular coils 12a, 12b, 14a, 14b, being distanced from each other along the x-direction to form substantially independent portions of the system 10 and having a rectangular shape when viewed along the x-direction. The rectangular shape has a longer side extending substantially along the z-direction. Additionally, the oppositely arranged substantially rectangular coils 12a, 12b, 14a, 14b are curved when viewed along the z-direction, i.e. the propagation direction P of the traveling field free line 16, to define oppositely arranged concave coil shapes.

Oppositely arranged coils can be in driven with opposite drive currents, such as to generate a magnetic field gradient along the x-direction. Each of the first and second coil assemblies 12, 14 may generate a first and second stationary field free line 16a, 16b extending along the y-direction at the first and second locations L1, L2, respectively, by driving a current through one of the coil assemblies 12, 14 and keeping the other one of the coil assemblies 12, 14 current free.

To generate a traveling field free line 16 traveling through the first and second locations L1, L2 at a middle position between the oppositely arranged substantially rectangular coils 12a, 12b, 14a, 14b, the driving currents in the first and second coil assemblies 12, 14 may be modulated with a periodic modulation function with a periodicity of $2\pi$, such as a sine function, wherein the respective drive currents of the first and second coil assemblies 12, 14 are phase shifted, such as by $\pi/2$.

With the deflection coil assembly 30 a deflection field may be generated to deflect the traveling field free line 16 in a deflection direction D different from the propagation direction P. For example, by driving the left and right portions of the deflection coil assembly 30 (according to the side view) as Maxwell coils and with opposite drive currents to generate a deflection field in the probe volume which is substantially oriented along the z-direction, the traveling field free line 16 may be deflected along the x-direction.

Hence, by modulating the currents in the first, second and deflection coil assemblies 12, 14, 30, a traveling field free line 16 may be generated at a desired position within a through-going passage 20 between the oppositely arranged substantially rectangular coils 12a, 12b, 14a, 14b.

The description of the preferred embodiments and the figures merely serve to illustrate the invention and the beneficial effects associated therewith, but should not be understood to imply any limitation. The scope of the invention is to be determined solely by the appended claims.

LIST OF REFERENCE SIGNS 10 system
12 first coil assembly
12a, 12b first, second portions/crossed coils of the first coil assembly
14 second coil assembly
14a, 14b first, second portions/crossed coils of the second coil assembly
15 additional coil assembly
16 traveling field free line
16a-16d first through fourth stationary field free lines
18 controller
18a-18c control paths
20 through-going passage
21 coil carrier
22 Maxwell coil assembly
24 first tilted Maxwell coil assembly
24a, 24b first, second coils of the first tilted Maxwell coil assembly
26 second tilted Maxwell coil assembly
26a, 26b first, second coils of the second tilted Maxwell coil assembly
28 traveling path of the traveling field free line
30 deflection coil assembly
32a, 32b first, second portions/crossed coils of the third coil assembly
34a, 34b first, second portions/crossed coils of the fourth coil assembly
35 cylindrical outer surface
36, 36a-36f anchoring points for the coil wire of the first coil assembly
37 anchoring points for the coil wire of the second coil assembly
38, 38a-38f anchoring points for the coil wire of the third coil assembly
39 anchoring points for the coil wire of the fourth coil assembly
40 stacked coil carrier assembly
41, 42 additional coil carriers
44, 45, 46 first through third crossed coils
S sample
P propagation direction
D deflection direction
B magnetic field
L1, L2, L3 first through third locations
$n_1$, $n_2$ normals
P1, P2 planes defining orientation of coils in the tilted Maxwell coil assemblies
x, y, z perpendicular directions of a coordinate system

The invention claimed is:

1. A system for generating a traveling field free line, traveling along a propagation direction different from the orientation of said traveling field free line, said system comprising at least a first and a second coil assembly,
   wherein said first coil assembly is configured for generating a first stationary field free line at a first location when a current is flowing in the first coil assembly and the second coil assembly is current free, and
   wherein said second coil assembly is configured for generating a second stationary field free line at a second location, when a current is flowing in the second coil assembly and the first coil assembly is current free,
   wherein said system further comprises a controller configured for driving the first and second coil assemblies with corresponding driving currents synchronized with each other such that:
      at a first point in time, the first coil assembly's driving current amplitude is high and the second coil assembly's driving current amplitude is low, such that at said first point in time the traveling field free line is at or close to said first location,
      at a second point in time, the second coil assembly's driving current amplitude is high and the first coil assembly's driving current amplitude is low, such that at said second point in time the traveling field free line is at or close to said second location, and
      in a time interval between said first and second point in time, the amplitude of the first driving current in the first coil assembly decreases and the amplitude of the second driving current in the second coil assembly increases as compared to said first point in time such that said traveling field free line travels along the propagation direction from said first location towards said second location.

2. The system according to claim 1, wherein between said first location and said second location the traveling field free line is translated along the propagation direction.

3. The system according to claim 1, further comprising a measurement coil for recording a non-linear response of an at least partially magnetizable system located in a probe volume between the first location and the second location to obtain a measurement of at least one of a density and a distribution of magnetizable particles in the at least partially magnetizable system.

4. The system according to claim 1, the system further comprising a third and a fourth coil assembly,
   wherein said third coil assembly is configured for generating a third stationary field free line at a third location, when a current is flowing in the third coil assembly and the first, second and fourth coil assemblies are current free,
   wherein said fourth coil assembly is configured for generating a fourth stationary field free line at a fourth location, when a current is flowing in the fourth coil assembly and the first, second and third coil assemblies are current free,
   wherein the first and third coil assemblies are arranged with respect to each other such that the first and third stationary field free lines form a nonzero angle,
   wherein the second and fourth coil assemblies are arranged with respect to each other such that the second and fourth stationary field free lines form a nonzero angle, and
   wherein said controller is configured to drive the first through fourth coil assemblies such as to generate a field free line at a desired position along the propagation direction and at a desired orientation.

5. The system according to claim 4, wherein the controller is further configured for inducing a helicoidal displacement of the traveling field free line by varying the respective current amplitude in a first pair of coil assemblies comprising the first and second coil assemblies and in a second pair of coil assemblies comprising the third and fourth coil assemblies, such that at times between said first and second point in time, the current amplitude in the first pair of coil assemblies is decreased and the current amplitude in the second pair of coil assemblies is increased.

6. The system according to claim 4, wherein the controller is further configured for varying the current amplitude $A_1$ in the first coil assembly according to $A_1 = a_1 * f_1^{\omega_1}(t) * f_2^{\omega_2}(t)$, varying the current amplitude $A_2$ in the second coil assembly according to $A_2 = a_2 * f_1^{\omega_1}(t+\varphi_1) * f_2^{\omega_2}(t)$, varying the current amplitude $A_3$ in the third coil assembly according to $A_3 = a_3 * f_3^{\omega_1}(t) * f_2^{\omega_2}(t+\varphi_3)$, and varying the current amplitude $A_4$ in the fourth coil assembly according to $A_4 = a_4 * f_3^{\omega_1}(t+\varphi_2) * f_2^{\omega_2}(t+\varphi_3)$, wherein $f_1^{\omega_1}$, $f_2^{\omega_2}$ and $f_3^{\omega_1}$ are periodic functions in time with a periodicity of $f_1^{\omega_1}$ and $f_3^{\omega_1}$ of $2\pi/\omega_1$, and a periodicity of $f_2^{\omega_2}$ of $2\pi/\omega_2$, and wherein $a_1$ to $a_4$ are proportionality constants, t relates to time, $\omega_1$ relates to a first frequency, the first frequency relating to a propagation time of the traveling field free line between the first and second location during a displacement of the traveling field free line along the propagation direction between the first and second point in time, $\omega_2$ relates to a second frequency, the second frequency relating to a rotation time of the traveling field free line about the propagation direction during the displacement of the traveling field free line along the propagation direction.

7. The system (44) according to claim 1, wherein the first and second stationary field free lines are oriented along a first radial direction with respect to said propagation direction, and wherein the third and fourth stationary field free lines are oriented along a second radial direction with respect to said propagation direction, and wherein the first and second radial directions form an angle deviating from 90° by less than 30°.

8. The system according to claim 1, further comprising a deflection coil assembly, the deflection coil assembly being adapted for generating a deflection magnetic field, wherein the controller is adapted to modulate the deflection magnetic field with a deflection frequency for displacing the traveling field free line along a radial direction, the radial direction being perpendicular to the traveling field free line.

9. The system according to claim 1, wherein the first coil assembly and the second coil assembly each comprise a first tilted Maxwell coil assembly, and a second tilted Maxwell coil assembly, said tilted Maxwell coil assemblies comprising two coils arranged in parallel planes and connected to be driven by opposite driving currents, said Maxwell coil assemblies defining a normal that is orthogonal to said parallel planes, wherein said first and second Maxwell coil assemblies are arranged such that the respective normals form a nonzero tilt angle with the propagation direction and are further arranged such that the normal of the first tilted Maxwell coil assembly and the normal of the second tilted Maxwell coil assembly form an angle, the angle being 90° or deviating from 90° by less than 45°.

10. The system of claim 9, wherein the system comprises a cylindrical coil carrier having an axis aligned with the propagation direction, wherein the coils of the first and second Maxwell coil assemblies are wound on the cylindrical coil carrier, and the first tilted Maxwell coil assembly and the second tilted Maxwell coil assembly share at least one common coil wire.

11. A method of generating a traveling field free line using at least a first and a second coil assembly, wherein said traveling field free line travels along a propagation direction different from the orientation of said traveling field free line wherein said first coil assembly is configured for generating a first stationary field free line at a first location when a current is flowing in the first coil assembly and the second coil assembly is current free, and wherein said second coil assembly is configured for generating a second stationary field free line at a second location, when a current is flowing in the second coil assembly and the first coil assembly is current free, the method comprising driving the first and second coil assemblies with corresponding driving currents synchronized with each other such that:

at a first point in time, the first coil assembly's driving current is high and the second coil assembly's driving current is low, such that at said first point in time the traveling field free line is at or close to said first location, at a second point in time, the second coil assembly's driving current is high and the first coil assembly's driving current is low, such that at said second point in time the traveling field free line is at or close to said second location, and in a time interval between said first and second point in time, the amplitude of the first driving current in the first coil assembly is decreased and the amplitude of the second driving current in the second coil assembly is increased as compared to said first point in time such that said traveling field free line travels along the propagation direction from said first location towards said second location.

12. The method according to claim 11, the method further using at least a third and a fourth coil assembly, wherein said third coil assembly is configured for generating a third stationary field free line at a third location, when a current is flowing in the third coil assembly and the first, second and fourth coil assemblies are current free, wherein said fourth coil assembly is configured for generating a fourth stationary field free line at a fourth location, when a current is flowing in the fourth coil assembly and the first, second and third coil assemblies are current free, wherein the first and third stationary field free lines form a nonzero angle, and wherein the second and fourth stationary field free lines form a nonzero angle, wherein the method further comprises driving the first through fourth coil assemblies such as to generate a field free line at a desired position along the propagation direction and at a desired orientation.

13. The method according to claim 11, the method further comprising generating a deflection magnetic field using a deflection coil assembly comprising a solenoid coil and varying the magnitude of the deflection magnetic field with a deflection frequency, to displace the traveling field free line in a radial direction perpendicular to the propagation direction.

14. The method according to claim 11, further comprising recording, with a measurement coil, a non-linear response of an at least partially magnetizable system located in a probe volume between the first location and the second location to obtain a measurement of a density and/or a distribution of magnetizable particles in the at least partially magnetizable system.

15. A computer program comprising machine readable instructions, which when executed, cause a computer to implement a method according to claim 11.

16. The system according to claim 4, wherein the first and third coil assemblies are arranged with respect to each other such that the first and third stationary field free lines form an angle deviating from 90° by less than 45, and wherein the second and fourth coil assemblies are arranged with respect to each other such that the second and fourth stationary field free lines form an angle deviating from 90° by less than 45°.

17. The system of claim 6, wherein $\varphi_1$ and $\varphi_2$ relate to phase shifts different from 0 and $\pi$, and wherein $\varphi_3$ relates to a phase shift different from 0 and $\pi$.

18. The system of claim 17, wherein $\varphi_1$ and $\varphi_2$ relate to phase shifts deviating from $\pi/4\omega_1$ by less than $\pi/4\omega_1$, and $\varphi_3$ relates to a phase shift deviating from $\pi/2\omega_2$ by less than $\pi/4\omega_2$.

19. The system according to claim 9, wherein said first and second Maxwell coil assemblies are arranged such that the normal of the first tilted Maxwell coil assembly and the normal of the second tilted Maxwell coil assembly form an angle, the angle deviating from 90° by less than 30°.

20. The method of claim 12, wherein the method further comprises inducing a helicoidal displacement of the traveling field free line by varying the respective current amplitude in a first pair of coil assemblies comprising the first and second coil assemblies and in a second pair of coil assemblies comprising the third and fourth coil assemblies, such that at times between said first and second point in time, the current amplitude in the first pair of coil assemblies is decreased and the current amplitude in the second pair of coil assemblies is increased.

* * * * *

UNITED STATES PATENT AND TRADEMARK OFFICE
CERTIFICATE OF CORRECTION

PATENT NO. : 11,382,526 B2
APPLICATION NO. : 17/041969
DATED : July 12, 2022
INVENTOR(S) : Patrick Vogel et al.

It is certified that error appears in the above-identified patent and that said Letters Patent is hereby corrected as shown below:

In the Specification

In Column 23, Line 26:
Replace "$f_1^{\ 1}$" with --$f_1^{\ \omega 1}$--

In Column 23, Line 42:
Delete "(44)"

In the Claims

In Column 26, Line 7:
Replace "$\pi/4\omega_1$" with --$\pi/2\omega_1$--

Signed and Sealed this
Twenty-fifth Day of October, 2022

Katherine Kelly Vidal
*Director of the United States Patent and Trademark Office*